(12) United States Patent
Cleverly et al.

(10) Patent No.: US 11,253,593 B2
(45) Date of Patent: Feb. 22, 2022

(54) GRANULATED ANTHELMINTIC PREPARATIONS AND DELIVERY SYSTEMS

(75) Inventors: Douglas Robert Cleverly, Auckland (NZ); Debashis Mukhopadhyay, Brockville Dunedin (NZ)

(73) Assignee: Argenta Innovation Limited, Auckland (NZ)

( * ) Notice: Subject to any disclaimer, the term of this patent is extended or adjusted under 35 U.S.C. 154(b) by 0 days.

(21) Appl. No.: 13/414,495

(22) Filed: Mar. 7, 2012

(65) Prior Publication Data

US 2012/0238516 A1 Sep. 20, 2012

Related U.S. Application Data

(63) Continuation-in-part of application No. PCT/IB2010/054005, filed on Sep. 7, 2010.

(30) Foreign Application Priority Data

| Sep. 7, 2009 | (NZ) | 579544 |
| Sep. 7, 2009 | (NZ) | 579545 |
| Sep. 7, 2009 | (NZ) | 579546 |

(51) Int. Cl.

| *A61K 45/06* | (2006.01) |
| *A61K 9/00* | (2006.01) |
| *A61K 31/4184* | (2006.01) |
| *A61K 31/425* | (2006.01) |
| *A61K 9/16* | (2006.01) |

(52) U.S. Cl.
CPC ............ *A61K 45/06* (2013.01); *A61K 9/0095* (2013.01); *A61K 9/1611* (2013.01); *A61K 9/1617* (2013.01); *A61K 31/4184* (2013.01); *A61K 31/425* (2013.01)

(58) Field of Classification Search
None
See application file for complete search history.

(56) References Cited

U.S. PATENT DOCUMENTS

| 3,626,070 | A | * | 12/1971 | Soboczenski | ........ C07D 235/32 514/388 |
| 8,372,415 | B2 | * | 2/2013 | Sun et al. | ...................... 424/400 |
| 2003/0055089 | A1 | * | 3/2003 | Sirinyan | ................ A01N 43/90 514/341 |
| 2004/0151759 | A1 | * | 8/2004 | Cleverly | .............. A61K 9/0056 424/442 |
| 2005/0226908 | A1 | | 10/2005 | Huron et al. | |
| 2006/0198850 | A1 | * | 9/2006 | Razzak | .............. A61K 31/7048 424/184.1 |
| 2011/0160218 | A1 | * | 6/2011 | Holmes et al. | ................ 514/250 |

FOREIGN PATENT DOCUMENTS

| GB | 2403407 | | 12/2006 |
| WO | WO 2000/074489 | | 12/2000 |
| WO | WO 2004/069242 | | 8/2004 |
| WO | WO 2005/016356 | | 2/2005 |
| WO | WO 2005016356 | A1 * | 2/2005 |
| WO | WO 2008/072985 | | 6/2008 |
| WO | WO 2009/060063 | | 5/2009 |

* cited by examiner

*Primary Examiner* — H. Sarah Park

(74) *Attorney, Agent, or Firm* — Tracey S. Truitt; Armstrong Teasdale LLP

(57) ABSTRACT

The present invention relates to anthelmintic compositions comprising two or more anthelmintic active agents selected from one or more of the following groups; imidazothiazoles such as levamisole, benzimidazoles such as oxfendazole, or fenbendazole, macrocylic lactones such as ivermectin or avermectin, salicylanilides, and praziquantel. The composition being in the form of stable granules that are readily dispersible in water so as to provide a homogenous mixture of the anthelmintic agents suitable for administration. Methods of preparing the composition are also described.

11 Claims, 5 Drawing Sheets

Chemical Stability – Levamisole HCl & Oxfendazole
(granule combination in Al Sachet Chemical Stability – Levamisole HCl & Albendazole
(granule combination in Al Sachet)

FIGURE 7

Process Flow Diagram - Liquid Suspension

FIGURE 8

Chemical Stability – Abamectin
(suspension concentrate in bottle)

GRANULATED ANTHELMINTIC PREPARATIONS AND DELIVERY SYSTEMS

INCORPORATION BY REFERENCE

This application is a continuation-in-part application of international patent application Serial No. PCT/M2010/054005 filed Sep. 7, 2010, which published as PCT Publication No. WO2011/027333 on Mar. 10, 2011, which claims benefit of New Zealand patent application Serial Nos. 579544, 579545 and 57954, all filed on Sep. 7, 2009.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to beneficial granules suitable as a platform technology for providing anthelmintic agents to animals.

More particularly the present invention relates to anthelmintic granules, kits involving packs of granules, methods of treating an animal using such granules, and methods of administering at least one anthelmintic active.

BACKGROUND OF THE INVENTION

U.S. Pat. No. 6,013,636 relates to ML anthelmintic actives such as avermectins, ivermectin, doramectin, abamectin, milbemycin and moxidectin and discusses that they are difficult to formulate. Reference is also made to injectable solutions, pour-on compositions and oral compositions formulations requiring not only a vegetable oil (such as soya bean oil, sesame oil and corn oil) but also a co-solvent which is an alcohol of 4 or more carbon atoms (eg benzyl alcohol).

WO 98/06407 (PCT/NZ97/00096) relates to an organic solvent able to dissolve both praziquanel and at least one ML anthelmintic as a pathway to a mixed phase packaged composition for direct oral administration to warm-blooded non-human animals. Most examples at manufacture may include an aqueous phase and a solvent phase. An example of a drench form without water has N-Methyl-2-Pyrrolidone present as a solvent.

WO 98/06407 relates to a nonaqueous injectable solution of abamectin and praziquantel used as manufactured (i.e. without further dilution).

WO 2004/009080 relates to an animal deliverable formulation capable of stably including avermectins or milbemycins together with levamisole. In reference to stability it is discussed that formulations have to be "stable" to be of commercial use. It is discussed that a commercially acceptable anthelmintic formulation as one which is "stable" at room temperature for a period of at least 6 months. It is reported that there is great difficulty in formulating such a combination product in order to achieve the required stability.

Reference is also made to the content of New Zealand patent specification 336139 of Nufarm pointing to the attempt to formulate a combination avermectin/milbemycin and levamisole product reliant upon emulsion technology.

The document mentions that to maintain stability of the avermectins and/or milbemycins in the presence of levamisole, it may be necessary to dissolve the actives in a pyrrolidone solvent, most preferably N-methyl pyrrolidone or 2-pyrrolidone.

Bomac in WO2008/072985 (PCT/NZ2007/000360) refers to a storage stable pour on veterinary formulation of an ML compound (optionally also with another active) in at least one glyceryl acetate solvent (optionally with co-solvents).

Embodiments of the present invention relate to on farm dilution allowing stable liquid formulations of ML actives to be made available and for customisation at dilution prior to administration. At the time of such dilution other components can be added and with the relatively brief time between dilution and administration stability becomes less of an issue. Certainly extended shelf life of an ML/BZ, ML/LEV and/or ML/BZ/LEV formulation can be rendered irrelevant while at the same time providing maximisation of customisation.

A further embodiment of the invention is to provide for fine ML particles or a ML present in a micro-emulsion in a final (and preferably customized) formulation including targeted on farm diluents(s) (whether water, aqueous, non-aqueous or other) having substantial homogeneity of particle spread and/or active spread.

A still further embodiment of the invention is to provide a low volume liquid concentrate of at least one ML anthelmintic active stable in that form for a satisfactory manufacture/supplier chain/user storage shelf life without substantial loss of ML and/or significant reduction in its dilutability.

A further embodiment is to provide a liquid concentrate of an ML able to be added to levamisole and/or a benzimidazole in water or an aqueous composition or a non-aqueous composition on farm just prior to administration.

A further embodiment is to provide at least substantially (and preferably) pyrrolidone free and/or glyceryl acetate free formulations of at least one ML active.

Citation or identification of any document in this application is not an admission that such document is available as prior art to the present invention.

SUMMARY OF THE INVENTION

Accordingly, in a first aspect the present invention relates to an anthelmintic composition in the form of a stable granule comprising two or more anthelmintic actives selected from but not limited to one or more imidazothiazoles, one or more benzimidazoles, one or more macrocyclic lactones, one or more salicylanilides, praziquantel, the stable granule being readily dispersible in water to provide a homogenous mixture of the anthelmintic actives for administration to a non-human mammal, the granule further comprising a suspending agent if the anthelmintic actives comprise a benzimidazole, a wetting agent if the anthelmintic actives comprise a macrocyclic lactone, a wetting agent if the anthelmintic actives comprise a salicylanilide and a suspending agent if the anthelmintic actives comprise praziquantel.

Another aspect of the invention relates to a dosage system for orally dosing animals with an anthelmintic agent, the system comprising
 (a) one or more packs of granules for addition into an aqueous liquid, the granules comprising
  (i) a benzimidazole and a suspending agent for the benzimidazole, (ii) a macrocyclic lactone and a wetting agent,
(iii) a salicylanilide and a wetting agent,
(iv) praziquantel and a wetting agent,
(v) an imidazothiazole and one or more anthelmintic agents selected from benzimidazoles, macrocyclic lactones, salicylanilides, and praziquantel, and optionally a suspending agent,
(b) a suspending agent if (i) the granules do not comprise a suspending agent, or (ii) additional suspending agent is required to suspend the anthelmintic actives in the liquid.

Another aspect of the invention relates to a method of preparing a stable liquid delivery formulation for treating an animal comprising the steps of
(a) providing one or more packs of granules, the granules comprising
 (i) a benzimidazole and a suspending agent for the benzimidazole,
 (ii) a macrocyclic lactone and a wetting agent,
 (iii) a salicylanilide and a wetting agent,
 (iv) praziquantel and a wetting agent,
 (v) an imidazothiazole and one or more anthelmintic agents selected from benzimidazoles, macrocyclic lactones, salicylanilides, and praziquantel, and optionally a suspending agent,
(b) adding the granules from the one or more packs of granules to an aqueous liquid,
(c) adding a suspending agent if (i) the granules do not comprise a suspending agent, or (ii) additional suspending agent is required to suspend the anthelmintic actives in the liquid.

Another aspect of the invention relates to a method of forming an anthelmintic composition comprising the steps of:
 providing two or more anthelmintic actives selected from one or more imidazothiazoles, one or more benzimidazoles, one or more macrocyclic lactones, and praziquantel,
 providing a suspending agent if the anthelmintic actives comprise a macrocyclic lactone,
 providing a wetting agent if the anthelmintic actives comprises a benzimidazole,
 mixing the macrocyclic lactone with the suspending agent if a macrocyclic lactone is present,
 mixing the benzimidazole with the wetting agent if a benzimidazole is present,
 combining the anthelmintic actives, and
 granulating the anthelmintic actives.

In one embodiment the method further comprises a step before the providing step of determining the treatment needs of one or more animals. Determination of the treatment needs of one or more animals can be carried out by a skilled worker with regard to that skill and the teaching of this specification.

In one embodiment the method further comprises administering the liquid to one or more animals. In another embodiment the method further comprises immediately administering the liquid to one or more animals.

Another aspect of the invention relates to a method of forming an anthelmintic composition comprising the steps of:
 providing an imidazothiazole,
 providing one or more anthelmintic actives selected from benzimidazoles and macrocyclic lactones,
 providing a suspending agent if the one or more anthelmintic active comprises a macrocyclic lactone
 providing a wetting agent if the one or more anthelmintic active comprises a benzimidazole
 mixing the macrocyclic lactone with the suspending agent if a macrocylic lactone is present,
 mixing the benzimidazole with the wetting agent if a benzimidazole is present,
 combining the anthelmintic actives, and
 granulating the mixture of anthelmintic actives.

The following embodiments may relate to any of the above aspects.

In some embodiments the imidazothiazole is levamisole HCL.

In some embodiments the composition comprises levamisole and a macrocyclic lactone. In some embodiments the composition comprises levamisole and a benzimidazole.

In some embodiments the composition comprises levamisole, a benzimidazole and a macrocyclic lactone.

In some embodiments the composition comprises a particulate source of one or more minerals. Unless where specifically stated, reference to minerals in this specification should be taken to be reference to any minerals required by the non-human animal to be treated, including but not limited to selenium, cobalt, magnesium, zinc, iodine and any combination of any two or more thereof.

In some embodiments the granules comprises a suspending agent.

In some embodiments the granules comprises a gum. Gums that may be useful in any embodiment described herein include but are not limited to agar, alginic acid, alginate, sodium alginate, carrageenan, arabic, ghatti, tragacanth, karaya, guar, locust bean, beta-glucan, chicle, dammar, glucomannan, mastic, psyllium seed husk, spruce, tara, gellan, and xanthan gums and any combination of any two or more thereof.

In some embodiments the granules comprises an anionic surfactant.

In some embodiments the granules comprise about 20, 25, 30, 35, 40, 45, 50, 55, 60, 65, 70, 75, 80, 85, 90 or 95% w/w of anthelmintic active.

In various embodiments, a composition useful herein may comprise about 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 or 99% w/w of one or more anthelmintic actives useful herein and useful ranges may be selected between any of these values (for example, about 1 to about 10, about 1 to about 20, about 1 to about 30, about 1 to about 40, about 1 to about 50, about 1 to about 60, about 1 to about 70, about 1 to about 80, about 1 to about 90, about 10 to about 20, about 10 to about 30, about 10 to about 40, about 10 to about 50, about 10 to about 60, about 10 to about 70, about 10 to about 80, about 10 to about 90, about 20 to about 30, about 20 to about 40, about 20 to about 50, about 20 to about 60, about 20 to about 70, about 20 to about 80, about 20 to about 90, about 30 to about 40, about 30 to about 50, about 30 to about 60, about 30 to about 70, about 30 to about 80, about 30 to about 90, about 40 to about 50, about 40 to about 60, about 40 to about 70, about 40 to about 80, about 40 to about 90, about 50 to about 60, about 50 to about 70, about 50 to about 80, about 50 to about 90, about 50 to about 60, about 50 to about 70, about 50 to about 80, about 50 to about 90, about 60 to about 70, about 60 to about 80, about 60 to about 90, about 70 to about 80, or about 70 to about 90). It should be understood that these values and ranges may relate to one anthelmintic active or a combination of anthelmintic actives. For example, a composition useful herein may comprise one, two, three or more anthelmintic actives and these values and ranges may relate to each active individually or to the combination of actives. Formulation of a particular combination of two or more actives can be carried out by a skilled worker with regard to that skill and the teaching of this specification.

In some embodiments the granule comprises less than 3, 2, 1% w/w water.

In some embodiments the granules are free or at least substantially free of pyrrolidones.

In some embodiments the composition comprises
from about 1 to about 40% w/w benzimidazole, and
from about 1 to about 70% w/w levamisole HCL.

In some embodiments the composition comprises 1, 5, 10, 15, 20, 25, 30, 35 or 40% w/w macrocyclic lactone.

In some embodiments the granules comprise a particulate thixotrope, particulate rheology modifier and/or gum.

In some embodiments the granules contain a suspending agent.

In some embodiments the suspending agent is added to the liquid.

In some embodiments the suspending agent is a gum.

In some embodiments the suspending agent of (a) (i) is a non-colloidal agent. In some embodiments the non-colloidal agent is silicon dioxide. In some embodiments the liquid is water.

In some embodiments the liquid is an anthelmintic concentrate.

In some embodiments the liquid contains avermectin and/or milbemycin in a liquid concentrate form.

In some embodiments the liquid delivery formulation is suitable for administration to animals for up to one month after mixing.

In some embodiments the granules comprise
from about 1 to about 40% w/w benzimidazole, and
from about 1 to about 60% w/w levamisole HCL.

Preferably the diluents is water or an aqueous composition.

Preferably xanthan gum is the or a thixotrope and/or suspending agent for a particulate BZ in the delivery liquid composition.

Preferably granules of at least one BZ and also containing LEV provide for a particulate BZ presence in the delivery liquid composition.

In an aspect the invention is a diagnosis of the anthelmintic needs of a herd of warm-blooded non-human animals and the provision of a corresponding kit of (ii) and/or (iii) type packs for use in a method as aforesaid.

In another aspect the invention is a use of one or more pack of granules and/or a liquid concentrate to provide for one or more of LEV, BZ and/or ML actives in a delivery liquid composition.

The present invention includes the use of dilutable powders, dilutable granules, and dilutable liquid concentrate(s) and/or semisolid concentrates to provide a multiactive anthelmintic formulation capable of oral, spray and/or topical delivery.

Preferably the granules at least in respect of one anthelmintic active result from a fluidized bed granulation of anthelmintic particles.

Various aspects of the present invention will now be described but not exclusively of other aspects as will be apparent from process flow diagrams, use diagrams and other aspects disclosed herein.

Optionally another anthelmintic (e.g. praziquantel) can be present in a granule, powder or liquid of the system.

Various anthelmintic actives have been considered for use in granules of the present invention. These include at least, by way of example, benzimidazoles such as oxfendazole, albendazole, fenbendazole, mebendazole, flubendazole, oxibendazole, triclabendazole, netobimin, thiabendazole, and febantel, salicylanilide such as closantal, brotianide, clioxanide, niclosamide, oxyclozanide, rafoxanide, bithionol, disophenol, hexachlorophene, nitroxynil, diamfenetid, and niclofolan menichlophola, imidazothiazoles such as levamisole HCL, levamisole base, pyrantel pamoate, butamisole, and tetramisol, and macrocyclic lactones such as abamectin, avermectin, moxidectin, doramectin, ivermectin, emamectin, eprinomectin, selamectin, milbemycin, and cydectin.

A preferment is both granules and powder(s) rather than just granules alone.

Preferably at least one benzimidazole is present in each granule.

Preferably a levamisole is present in each granule or some granule(s).

The other inclusion preferably include a gum as a athixotrope.

Preferably a gum is present as a suspending agent for at least the benzimidazole content whereby, when diluted, there will be substantial homogeneity of the resultant suspension.

Preferably the anthelmintic agent(s) of each granule accounts for at least about 30% w/w (more preferably at least about 40% w/w) (still more preferably at least about 50% w/w) (and most preferably from about 40% w/w to about 70% w/w) of the granule weight.

Preferably the granules have less than about 3% w/w (more preferably less than about 2% w/w) of water.

Preferably the granules are free or at least substantially free of water.

Preferably the granules are free or at least substantially free of pyrrolidones.

Preferably a non-aqueous liquid is present in the anthelmintic granules in the range up to about 20% w/w of the granule (preferably at least about 10% w/w).

Most preferably some water is present and some non-aqueous liquid is present in the anthelmintic granules.

Preferably any alcohol (e.g. benzyl alcohol) is present in an amount less than that needed to dissolve all of any anthelmintic active present.

Whilst they can be prepared by any granulation technique (these techniques include but are not limited to single pot granulation, fluid bed top spray granulation, high sheer granulation/fluid bed drying combination, continuous fluid bed granulation, spray drying, etc), preferably the granules, at least in respect of one anthelmintic active, result from a fluidized bed granulation reliant on spraying of a solids stream that includes the anthelmintic particles. Dry compaction (dry granulation) and wet extrusion followed by drying and sizing may be used.

By way of example only a preferred double anthelmintic active granule can have:

| QUANTITY | FUNCTIONALITY | A PREFERENCE |
|---|---|---|
| 10 to 40% $^w/_w$ | a benzimidazole | Oxfendazole or albendazole about 15 to about 25% $^w/_w$ |
| 10 to 60% $^w/_w$ | levamisole HCl | about 30 to about 40% $^w/_w$ |

A suitable levamisole is levamisole HCl.

Suitable benzimidazole(s) include those sparingly soluble in water.

Examples include but are not limited to oxfendazole, albendazole, fenbendazole, mebendazole, flubendazole, oxibendazole, triclabendazole, netobimin, thiabendazole, febantel, etc.

Most preferably the BZ is oxfendazole, albendazole or fenbendazole.

Praziquantel might also be included in granule(s) powder(s).

Preferably a benzimidazole active ingredient is suspendable.

Preferably the suspendable anthelmintic particles are no larger than those of that anthelmintic actives starting material particles.

Preferably a levamisole active ingredient is present.

Optionally granulation involves one or more sprays of a solids stream on a fluidized bed.

A spray may involve a liquid antifoaming agent and/or minerals and/or vitamins.

A spray may involved a liquid in which the benzimidazole is more soluble than it is in water but in insufficient quantity to fully dissolve the benzimidazole starting material(s).

A spray may involve a ML (Milbemycin).

In another aspect the invention is a dosage system for orally dosing animals with at least one beneficial agent (preferably at least one anthelmintic active), said system requiring
(a) one or more packs of granules of the beneficial agent(s) of the present invention, and
(b)
  (i) a drenching device and a mixing container, or
  (ii) a drenching device having a mixing reservoir,
when one or other, or both, (A) and/or (B) is in physical association with instructions whereby use of
(a) the one or more packs
(b) a said mixing container or said mixing reservoir with water or a aqueous carrier as instructed in, and
(c) the drenching device for its fixed dosage amounts or a calibratable variable dosage amount,
will deliver, in use, an effective amount of the beneficial agent(s) to each drenched target animal.

In another aspect the invention is a dosage system for orally dosing animals with plural anthelmintic actives, said system comprising or including
(a) one or more packs of granules of at least one anthelmintic active of the present invention, and
(b) at least one container with an avermectin and/or milbemycin active in a liquid concentrate form
(c)
  (i) a drenching device and a mixing container, or
  (ii) a drenching device having a mixing reservoir,
when one or more of (A), (B) and/or (C) is in physical association with instructions whereby use of
(a) all of one or more pack content(s),
(b) all of one or more container content(s),
(c) the mixing container or mixing reservoir with water or an aqueous carrier as instructed, and
(d) the drenching device for its fixed dosage amounts or its calibratable variable amount,
will deliver, in use, an effective amount of the plural anthelmintic agents to each drenched target animal.

In another aspect the invention is the use of a pack or quantity of anthelmintic granules to deliver a recommended dose orally per animal when diluted with water or other aqueous carrier as instructed, the granules being readily associable with the water or aqueous carrier.

In another aspect the invention is a method of treating an animal which comprises or includes, in any order (A (i) to A (iv)):
(a) (i) providing or taking at least one volume of anthelmintic granules [preferably of substantial homogeneity] able to be associated (eg, by dispersion) with water or an aqueous composition to provide a (preferably thixotropic or pseudoplastic) liquid composition containing one or more anthelmintic actives,
   (optionally (ii) providing or taking a liquid concentrate of at least one avermectin and/or at least one milbemycin),
   (iii) providing or taking a volume of water and/or an aqueous composition, and
   (iv) providing or taking apparatus able to administer a (preferably thixotropic) liquid composition to such an animal; and
(b) associating in any order (i) and (iii) or (i), (ii) and (iii), whether in the apparatus of A(iv) or not; and
(c) using the apparatus of A(iv) to administer the (preferably thixotropic or pseudoplastic) aqueous composition resulting from (B) to such an animal.

In another aspect the invention is a method of administering a mix of anthelmintic actives to an animal which comprises
(1) preparing an aqueous delivery composition
   (a) from a dry granular composition of at least one anthelmintic active of the present invention, or
   (b) from both a dry composition of at least one anthelmintic active of the present invention and a liquid concentrate of at least one other anthelmintic active, and
(2) administering an effective amount of the aqueous delivery composition to the animal.

In an aspect the invention is an on-farm preparation for administration to an animal, the preparation being an aqueous suspension of ML anthelmintic particles derived from a non-aqueous concentrate upon its aqueous dilution, the concentrate not necessarily (and preferably not) having the ML antibiotic present in a particulate form.

Preferably a gum suspends the particles, the gum being derived from the concentrate.

Preferably the administration is to be by any of the routes herein described.

In another aspect the invention is an on-farm preparation as aforesaid that includes other components added in a substantially dry form.

In yet another aspect the invention is an on-farm anthelmintic preparation prepared by dilution of a concentrate in a liquid or gel form of at least one ML anthelmintic active.

Preferably the concentrate is as herein described.

Optionally the dilution is with water, an aqueous composition or a non-aqueous liquid.

In another aspect the invention is at least one pack of granules of at least one anthelmintic active for use in an, on farm, customisation of a liquid delivery formulation of beneficial agents to animals.

In another aspect the invention is a webcast, website, blog, flyer, brochure, datasheet or other (substrated) material(s) providing or extolling the ability or virtue of granules (eg as defined herein) and/or liquid concentrate(s) (eg as defined in our patent application(s) filed simultaneously herewith) and/or dispensing apparatus in respect of the administration of one or more beneficial agent (eg to a target species animal type).

Another choice of course are liquid or semisolid (e.g. gel) preparations (and particularly concentrates) for a targeted diluent type. In particular, although not solely, the invention relates to stable liquid concentrates of at least one ML active (i.e., Macrocyclic Lactone anthelmintic active(s)).

The present invention relates to a product, the whole content of which, is to be on farm diluted (e.g. water or oil dilution) for animal administration. This may maximize shelf-life and availability of the active(s) as well as allowing customisation at the dilution stage of the active(s) and beneficial agents to be administered.

Applicants assert that on farm dilution allows stable liquid or semisolid formulations of ML actives to be made available with a shelf life or at least about 6 months and for customisation at dilution prior to administration. At the time of such dilution other components can be added and with the relatively brief time between dilution and administration stability becomes less of an issue. Certainly extended shelf life of an ML/BZ, ML/LEV and/or ML/BZ/LEV formulation can be rendered irrelevant while at the same time providing maximisation of customisation.

Aspects of the invention relate to providing a contained stable anthelmintic liquid or semi solid concentrate targeted for dilution prior to animal administration, the concentrate being a solution, emulsion, microemulsion, micronized suspension, nanonized suspension, or some combination thereof;
  wherein at least one ML anthelmintic is present in (i) a water miscible organic solvent and/or (ii) an oil or organic liquid miscible type solvent;
  and wherein at least one non ML anthelmintic agent and/or other beneficial component(s) may be present;
  and wherein a gum or alginate, or both, is present;
  and wherein chelating agent(s), stabilizer(s), etc may be present;
  and wherein the whole concentrate content of the container of the concentrate is for dilution prior to animal administration.

Preferably the concentrate is liquid.

Preferably the concentrate is free of pyrrolidone solvent and/or is free of glyceryl acetate solvent.

Aspects of the invention relate to both high gum and low gum formulations, low gum being below 5% W/W, and high gum 5% w/w (e.g. 5-20% w/w) Gums can be Xanthan. Alginates of different viscosity grades may be used.

Preferably the gum provides a thixotropic mix when diluted.

Another prospect is a storage stable and contained liquid or gel formulation (eg a liquid concentrator a gelled concentrate) of at least one ML anthelmintic active for dilution in a diluent, to provide a deliverable composition, prior to administration (orally, as a pour on and/or as a spray or dip) to a target species of animal:
  wherein the ML active(s) is at least substantially stable in its concentrate liquid or gel environment.

The ML active(s) can be more stable in the concentrate than were it to be already diluted with the intended diluents(s), yet is readily mixable with such a diluent prior to administration.

Preferably the formulation is for a target diluent (includes a range of diluents) and the formulation is or includes:
  (i) at least one ML active,
  (ii) an organic solvent or organic solvents in which the ML active(s) is (are) stable, and
  (iii) at least one suspending agent, whereby, when in the or a targeted diluents(s), the at least one ML active, as a precipitate or as a microemulsion, will be suspended.

The formulation is ideally at least almost totally non-aqueous.

Preferably where the diluent is, or is to be, water or an aqueous composition.

Preferably said solvent is water miscible.

In other embodiments the diluent is, or is to be, an organic vehicle such as one or more vegetable oil (e.g. soya bean, sesame oil, corn oil, etc)

Preferably said solvent is vegetable oil miscible.

Preferably the ML active is selected from the group consisting of avermectins and milbemycins eg more preferably is one or more of abamectin, moxidectin, doramectin, ivermectin, emamectin.

Preferably the concentrate is free of pyrrolidone solvent and/or is free of glyceryl acetate solvent.

Further aspects of the invention also relate to a stable liquid concentrate in a container or pack and intended for aqueous dilution to an anthelmintic delivery or dosage form, the concentrate comprising or including at least one ML anthelmintic active,
  an organic solvent of the ML active(s), and
  a suspending agent able to suspend the ML active(s) in the aqueous diluents(s) (even if water rather than an aqueous composition);
  and optionally a preservative;
  and optionally an antifoam agent to reduce foaming on aqueous dilutions,
  and optionally a bulking agent.

Benzyl alcohol is a preferred preservative.

Polysorbate80™ is a preferred surfactant/antifoam agent. Sodium lauryl sulphate is another option. A molten wax may also be present.

Fumed silicon dioxide is a preferred building agent.

Preferably the concentrate is free of pyrrolidone solvent and/or is free of glyceryl acetate solvent.

Another option is a stable liquid concentrate in a container or pack and intended for non-aqueous dilution to an anthelmintic delivery or dosage form, the concentrate comprising or including
  at least one ML anthelmintic active,
  an organic solvent of the ML active(s), and
  a suspending agent able to suspend the ML active(s) in the non-aqueous diluents.

Preferably the solvent is one or more glycol ether, and/or one or more cyclic-ether.

A preferred solvent is glycerol formal, propylene glycol or glycerol formal and propylene glycol. Another water miscible solvent option (alone or with any other) is glycerine.

A particularly preferred solvent is glycerol formal.

A preferred suspending agent for a non-aqueous diluent (e.g. a vegetable oil) is as mentioned above.

Preferably the concentrate is free of pyrrolidone solvent and/or is free of glyceryl acetate solvent.

Yet another option is a liquid concentrate in the form of a solution, the solution having
  (a) at least one ML active
  (b) at least one organic solvent in which the ML active(s) is (are) stable, and
  (c) at least one gum as suspending agent, whereby in water or an aqueous composition with which it is suitable for dilution, the at least one ML active, as a precipitate, will be suspended or be dispersed (e.g. as in a fire emulsion) and the aqueous suspension, dispersion or emulsion is suitable for administration to an animal orally, as a pour-on or as a spray or dip formulation.

Microemulsions are preferred as a pour-on.

Optionally the liquid concentrate includes a glycol ether or cyclic ether as the solubilizer and/or stabilizer, or at least one said organic solvent.

A preferred solvent is glycerol formal, propylene glycol or glycerol formal and propylene glycol.

Preferably said ML active is one or more of an abamectin, moxidectin, doramectin, ivermectin, emamectin etc.

Preferably said solvent is one or more glycol ether and/or cyclic ether. The solvent is preferably glycerol formal.

Preferably the liquid concentrate includes an antifoam agent.

Preferably a preservative and a bulking agent is also present.

A preferred preservative is benzyl alcohol also able to act as a co-solvent.

A preferred bulking agent is fumed silicon dioxide.

A preferred suspending agent for a non-aqueous diluents (e.g. a vegetable oil) is as mentioned above.

Preferably the concentrate is free of pyrrolidone solvent and/or is free of glyceryl acetate solvent.

Aspects of the invention relate to a container in which a liquid concentrate is a formulation as previously defined, and associated with instructions as to dilution prior to administration to an animal.

Aspects of the invention relate to an on-farm preparation for administration to an animal, the preparation being an aqueous suspension of ML anthelmintic particles derived from a non-aqueous concentrate upon its aqueous dilution, the concentrate not necessarily (and preferably not) having the ML anthelmintic present in a particulate form.

Preferably a gum suspends the particles, the gum being derived from the concentrate.

Preferably the administration is to be by any of the routes herein described.

Aspects of the invention also relate to an on-farm preparation as aforesaid that includes other components added in a substantially dry form.

Aspects of the invention relate to an on-farm anthelmintic preparation prepared by dilution of a concentrate in a liquid or gel form of at least one ML anthelmintic active.

In another aspect the invention is a webcast, website, blog, flyer, brochure, datasheet or other (substrated) materials providing or extolling the ability or virtue of granules and/or granules and powders and/or liquid and/or semisolid concentrate(s) and/or dispensing apparatus in respect of the administration of one or more beneficial agent (e.g. to a target species animal type).

As used herein "diluent", "target diluents", etc preferably (but not necessarily) refers to a diluent with which a liquid content of the concentrate granule(s) is miscible.

As used herein "LEV" means a levamisole and "BZ" means a benzimidazole.

As used herein "semisolid" envisages gelled or other such forms, as a mass whether pourable or not, able to be diluted with the target diluent type.

As used herein "on-farm" or the equivalent can mean in close time proximity for use with the animals e.g. A veterinarian may dilute a customized selection of concentrate(s), granules and/or powder(s) for a farmer.

Reference to "animal(s)" preferably includes any suitable animal, warmblooded or not, farmed, domestic, companion or other (ruminant or otherwise and can include fish).

Reference to "beneficial agent(s)" includes but is not restricted to trace elements and vitamins. It can include anti-bloat agents, digestion ads, growth promotants, etc.

As used herein the term "and/or" means "and" or "or", or both.

As used herein "(s)" following a noun means the plural and/or singular forms of the noun.

Reference to "animal(s)" preferably includes any suitable warm-blooded animal ruminant or otherwise.

Reference to "beneficial agent(s)" includes but is not restricted to trace elements and vitamins. It can include anti-bloat agents, digestion ads, growth promotants, etc.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 7 is one of several flow diagrams able to produce a liquid concentrate as described, such a formulation being exemplified, by way of example, by Example 12 hereafter.

FIG. 8 shows the stability of a concentrate as in Example 12 in a typical bottle (by way of example, a glass or plastic bottle (HDPE or other))

DETAILED DESCRIPTION

Figure 1:
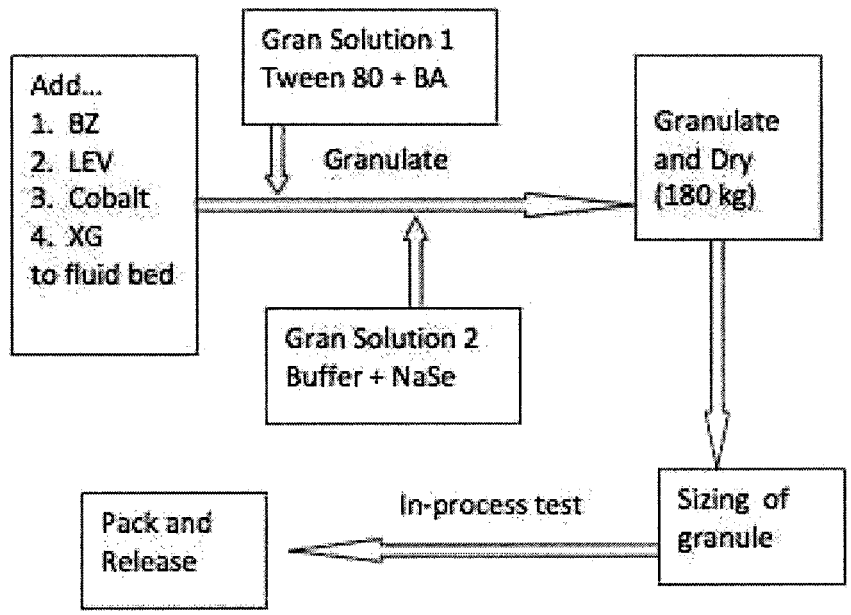
FIG. 1 is one of several flow diagrams able to produce granules as described, such a formulation being exemplified hereafter (NB Granulation Solution 1 may or may not include a drug, anthelmintic and/or beneficial agent(s))

The present invention recognizes that for many purposes animal health products are supplied in formulations that are greater than 80% water or other diluent.

The present invention recognizes the advantage to be derived for many situations where anthelmintic and/or beneficial agents are to be administered or self administered ("administered") to an animal (warmblooded or not farm animals, companion animals, fish, etc) to provide a platform that obviates the need of the provision through from manufacture to end user of unnecessary water and/or other liquid carrier(s).

The present invention in addition or instead recognizes that for some beneficial agents, there are advantages insofar as transport, storage and inventory costs are concerned of having beneficial agents provided in a form able to be readily associated with water or other diluent (without a requirement of specialist mixing equipment) prior to administration to an animal.

In many instances there are single or combinations of beneficial agents that advantageously can be maintained in association in at least substantially fixed proportions without the instability sometimes encountered in liquid formulations.

By way of example, the present invention recognizes how single or a combination or combinations of anthelmintic actives can be combined into a granular product (whether in each individual granule or in blends of different granules) advantageously (or both granules and powder forms) with respect to the advantages discussed as well as not being significantly detrimental to end usage and/or stability during storage. Indeed for some such formulations, preferably in a simple or complex granular form, there are stability advantages over having one or more of the actives in a simple liquid formulations.

Such single or combined anthelmintic actives (granulated, granulated and powder, and/or liquid concentrate) can be directly or indirectly associated with mineral supplements and vitamins either in the granule itself and/or in ancillary concentrated forms to be associated with the anthelmintic active or actives when downstream (eg with the farmer) in a delivery or dosage liquid formulation.

Various anthelmintic actives have been considered for use in the platform technology of the present invention, these include by way, of example, in granulated form benzimidazole(s) typified by oxfendazole, albendazole, etc and levamisole(s) typified by its variations including levamisole, base levamisole HCl or any of its salts.

Praziquantel and MLs are another possibility.

Typical of anthelmintic actives that lend themselves to a liquid concentrate are ivermectins and milbemycins (eg abamectin, ivermectin, etc).

Beneficial agents considered in respect of the platform technology and related aspects of the present invention include mineral supplements, vitamins, etc.

Target species include farmed or unfarmed animals, domestic or companion animals (e.g. cattle, sheep, horses, deer, swine, dogs, cats, fish etc). The invention is preferably for use with target ruminants being farmed where significant quantities can be diluted for serial animal administration. This enables on farm customisation of beneficial agents in a liquid mix (preferably aqueous) prepared immediately or soon prior to administration.

Such beneficial agents preferably include trace element additions (e.g. selenium, magnesium, cobalt, zinc, iodine, etc) and/or vitamins or vitamin precursors.

Suitable suspending agents include one or more of
gums (such as xanthan, guar, gellan, etc)
fumed or colloidal silicon dioxides (eg AEROSIL R972®, AEROSIL 200 Mesh, etc)
THIXCIN® (a nonhydroscopic castorwax derivative of castor oil).

A most preferred suspending agent is particulate xanthan gum either in the dry mix to be granulated by any process or in the dry mix and/or granulating fluid of a fluidized bed granulation process.

Such beneficial agents can include or be added using anthelmintic liquid concentrate additions.

Preparation of dual anthelmintic active granules and with a cobalt and selenium source as further beneficial agents can be prepared as in FIG. 1 which shows a fluidized bed top spray granulation process using two sprays in series.

A solids stream of particulate benzimidazole(s) ("BZ"), a levamisole ("LEV"), a cobalt source ("Cobalt") and xanthan gum ("XG") is fed to the fluidized bed.

First a granulating solution of Tween 80 and benzyl alcohol ("BA") is sprayed. This may or may not have any active in a fully or partially dissolved. Second a granulating solution of a buffer and a selenium source (NaSe).

This leads then the granules being formed and dried prior to sizing and packing e.g. in plastic, aluminium or like bags, containers, etc.

Suitable applicators for administering the deliver composition are those available from N J Phillips Pty Limited, Instrument Supplies Ltd, Simcrotech Ltd and PrimaTech Ltd. Particularly preferred are backpack reservoired applicators of N J Phillips Pty Limited (e.g. with 2.5 litre backpack) and a variable dose capability.

Liquid impregnated granules optionally can be one of the following:
It can be mixture of a Liquid Surfactant and a liquid preservative (e.g. Polysornate 80 and Benzyl Alcohol)
It can be a mixture of a Liquid surfactant/s+Solvent (usually water miscible type but not limited to e.g. glycerol formal, Propylene glycol)+Liquid or a solid Preservative.

Usually below 10% w/w low liquid content granules and above 10% w/w is regarded as high liquid content granules. Liquid's are described above. Usually these liquid impregnated granules contain a potent organic soluble drug/s e.g. Abamectin not limited to ML can be any organic drug, beneficial chemical agent.

The drugs may be in a solubilized state or a partially solubilized state (which reduces the particle size of the drug).

The aim of impregnating granules is to make the granules function as a liquid and as a solid. The liquid part after coming in contact with the reconstitution medium either precipitates the drug as a fine suspension or may form a micro-emulsion or even a coarse emulsion (i.e. thermodynamically unstable).

Addition of water miscible components can lower the freezing point of the reconstituted formulation if water is to be used as a reconstituting medium.

1. Multi-Active Granules

In some embodiments the invention consists in anthelmintic granules (preferably of substantial homogeneity notwithstanding historical particles may still be manifest in part in the granules) able to be associated (e.g., by dispersion) with water or an aqueous composition to provide a [preferably thixotropic or pseudoplastic] liquid composition able to be administered (e.g. mechanically administered, or able to be self administered), to an animal or to animals, the granules being of, or derived from, at least
(a) from about 1 to about 70% w/w of at least one particulate anthelmintic active
(b) from about 0 to about 20% w/w of at least one particulate beneficial agent
(c) from about 1 to about 10% w/w of a particulate thixotrope, particulate rheology modifier and/or gum.

In another embodiment the composition is, or is formulated as, an anthelmintic granules, preferably of substantial homogeneity notwithstanding historical particles may still be manifest in part in the granules, that is able to be associated (e.g. by dispersion) with water or an aqueous composition to provide a liquid composition able to be administered (e.g. mechanically administered, or able to be self administered), to an animal or to animals, the granules being of, or derived from, at least
(a) from about 1 to about 20% w/w of at least one particulate anthelmintic active
(b) from about 0 to about 20% w/w of at least one particulate beneficial agent
(c) from about 1 to about 10% w/w of a particulate thixotrope, particulate rheology modifier and/or gum. Preferably the composition is thixotropic or pseudoplastic.

In another embodiment the composition is a granulated product capable of dilution to a delivery composition form to which other active(s) and/or beneficial agent(s) might also have been, be or are to be added, the product being
(a) produced substantially as herein described or analogously thereto, OR
(b) substantially as herein defined or exemplified, or analogous thereto, OR
(c) having a combined deliverable content of anthelmintic active(s) post agglomeration or granulation from particles of at least 30% w/w (and preferably higher).

In another embodiment the composition is an oral dosage aqueous composition having present one or both:
(a) at least one or two anthelmintic actives derived from a pack of granules of such actives, and
(b) at least one anthelmintic active derived from a container of a liquid or semisolid
(c) concentrate of that anthelmintic active.

Preferred anthelmintic granules include able to be associated with water or an aqueous composition to provide a liquid composition able to be administered (mechanical administered, or able to be self administered), to an animal or to animals, the granules being of at least
(a) from about 1 to about 30% w/w of at least one anthelmintic active, and
(b) from about 0 to about 20% w/w of at least one beneficial agent, and
(c) Up to about 80% w/w of other inclusion(s).

In another embodiment the composition consists in granules, or a blend of granules, having one or more benzimidazole, a levamisole, or both, in individual granules wherein the granules can release into diluent water or an aqueous diluent composition
(a) particles of said at least one benzimidazole, and
(b) sufficient suspending agent(s) to hold the benzimidazole particles at substantial homogeneity.

In another embodiment the composition consists in anthelmintic granules able to be associated with water or an aqueous composition to provide a liquid composition able to be administered (mechanical administered or able to be self administered), to an animal or to animals, the granules being of at least
(a) from 1 to 30% w/w of at least one anthelmintic active,
(b) from 0 to 20% w/w of at least one beneficial agent, and
(c) up to 80% w/w of other inclusion(s).

In another embodiment the anthelmintic granules has at least both some liquid content and anthelmintic content and having an ability of being converted for liquid carried animal administration with a diluent.

In some embodiments the invention is, as a dilutable source of at least one anthelmintic active, are granules of at least one anthelmintic agent (preferably two but optionally three or more) optionally having other beneficial agent inclusions, or being in admixture with one or more powdered and/or granulated source of other agent (e.g. anthelmintic, beneficial or other); wherein one or more of the following applies
a benzimidazole is present,
a levamisole is present
an ML anthelmintic is present
a gum or other particle suspension agent effective upon aqueous dilution is present
an at least substantially homogeneous suspension of at least one anthelmintic agent can be created with aqueous dilution
an at least substantially homogeneous diluted composition can be created by non-aqueous dilution (e.g. with a suitable oil, alcohol and/or glycol).
a particulate source of one or more mineral is present
selenium particles are present
water is absent or below 3% w/w of the granules is present in the granules
a liquid other than water of from about 5 to about 20% w/w (preferably about 10 to about 20% w/w)
an inclusion of the granules has been microencapsulated
an anionic surfactant is present in the granules
the granules, or granules and other powdered and/or granulated material, is packed to a volume of from about 100 to about 600 ml (more preferably about 200 to about 400 ml).

In some embodiments the invention is an anthelmintic granules or a blend of anthelmintic granules to provide a benzimidazole active or both a benzimidazole active and a levamisole active, the granules having a suspending agent for at least most of the benzimidazole content if and when released into water or an aqueous diluent, and optionally with other inclusions; wherein all or some of the granules have an anthelmintic active content of from about 20 to about 80% w/w.

In some embodiments the invention is anthelmintic granules having an anthelmintic content (whether of one or more anthelmintic actives) of at least about 30% w/w and having been formed by a granulation process in which one or more anthelmintic active(s) has (have) been presented as particulate starting material(s);

wherein the granulation process has involved at least a suspending agent;

and wherein, upon delivery dilution prior to administration to a warm-blooded animal, the suspending agent will suspend particles of at least one granule included anthelmintic active ingredient.

Without wishing to be tied to a theory, anthelmintic actives in a granule or a mix of anthelmintic actives in a granule, where the matrix of the granule(s) includes carrier materials (which can be other beneficial agent(s)) not conducive to chemical and/or physical instability of the anthelmintic active(s) reduces the within granule and/or granule to granule interface of the different anthelmintic actives. Similarly where a pack (e.g. a sachet) might contain at least one granule type whether with or without any other particulate content (e.g. powdered anthelmintic active, vitamins, minerals, etc).

For benzimidazole(s) and levamisole a suspending agent such as a gum can be used in the matrix. Likewise other inclusions that can be conducive to performance post dilution with a target or non-targeted diluent, and/or prior dilution with a targeted or non-targeted diluent, and/or to deliver other beneficial agents to the recipient(s). For example a suspending agent suitable in a diluent that is nonaqueous such as castor oil or soya oil or other thick oil. For example a suspending agent suitable for aqueous dilution.

In some embodiments the granules remain stable for at least one month.

In some embodiments the granules remain stable for at least 2, 3, 4, 5, or 6 months.

In some embodiments the granule comprises about 25 to about 50% imidazothiazoles.

In some embodiments the granule comprises about 15 to about 50% benzimidazole.

In some embodiments the granule comprises about 10 to about 25% praziquantal.

In some embodiments the granule comprises about 0.10 to about 10% macrocyclic lactone.

In some embodiments the benzimidazoles is selected form one or more of oxfendazole, albendazole, fenbendazole, mebendazole, flubendazole, oxibendazole, triclabendazole, netobimin, thiabendazole, and febantel.

In some embodiments the salicylanilide is selected form one or more of closantal, brotianide, clioxanide, niclosamide, oxyclozanide, rafoxanide, bithionol, disophenol, hexachlorophene, nitroxynil, diamfenetid, and niclofolan menichlophola.

In some embodiments the imidazothiazoles is selected form one or more of levamisole HCL, levamisole base, pyrantel pamoate, butamisole, and tetramisol In some embodiments the macrocyclic lactones is selected form one or more of abamectin, avermectin, moxidectin, doramectin, ivermectin, emamectin, eprinomectin, selamectin, milbemycin, and cydectin.

2. Stable Liquid Delivery

In some embodiments the invention is an agglomeration of benzimidazole and levamisole particles without any substantial or full dissolution of either species of particle and in the presence of a suspending agent effective
   (a) upon dilution with water or an aqueous composition of suspending evolved benzimidazole particles, or
   (b) upon dilution with a solvent for the benzimidazole, to suspend the evolved levamisole particles, or
   (c) upon dilution with an organic liquid to suspend any evolved particles in that organic liquid.

Preferably, if (a), the suspending agent is a gum such as xanthan gum.

If (b) or (c), preferably an alcohol is present at dilution, or, more preferably a vegetable oil is present at dilution.

In some embodiments the packs of granules or granules and powder(s) are emptied for dilution into a delivery system reservoir dilution to a delivery system reservoir volume. Likewise any liquid or semisolid concentrate.

In some embodiments the invention is an anthelmintic delivery liquid composition having BZ particles derived from granules of at least one BZ active or both at least one BZ active and a LEV active suspended in an aqueous carrier or water, the suspension agent being at least in part derived from the granules.

In some embodiments the composition also includes an ML active made available to the remainder of the delivery liquid composition from a liquid concentrate of the ML active.

In some embodiments the liquid concentrate has the ML active carried (at least in part) in an organic liquid or in organic liquids.

3. Method of Manufacturing a Granule

In some embodiments the granules for aqueous and/or nonaqueous dilution for oral dosing purposes(s), have been prepared by a process wherein:
   1. a particulate anthelmintic agent or particulate anthelmintic agents (and optionally one or more other particulate beneficial agent(s)) and at least one particulate suspending agent and/or rheology modifier and/or gum is provided on a fluidized bed, and
   2. one or more liquid composition(s) adding to the solids on the fluidized bed to provide the resultant granules.

Powder type: Mix the drug/s (bulky drugs) either in a suitable mixer with other ingredients. In some cases the mixing might be done in a high shear mixer or a ball mill. The powders may be compacted i.e. dry granulated if flow problems arise.

Granule type: a dry mix of powders will be granulated using one or more granulating fluids. In some cases ball milled powders may be used for granulation in a wet/dry granulator.

Hybrid type: Part of the formulation may be granulated (wet or dry) and part of it may be mixed in a suitable mixer. Essentially it is a mix of the other two types indicated above. This helps in avoiding full batch granulation saving on processing costs.

Other special cases: Microcapsules or pellets may be loaded to the granule platform if need arise. Relevant processes apply under those circumstances.

Note: The choice of process will depend on the type of formulation.

Formulation Presentation Notes

The final granule or powder formulation may be sold as sachet pack/s or may be sold as capsules. Kit will contain items like spray guns/capsule delivery systems e.g. capsule gun. Incompatible drugs may be packed separately as sachets.

Sachet pack (Liquid Product): Granules/powders etc discussed till now may be dispensed in one or more sachets. The following are some of the options but not exhaustive.

Capsule type: The granules/powders may be filled in hard capsules which may or may not contain drug contain. They may include flavor enhancing chemicals.

Indeed flavor enhancing chemical(s) can be added to granules and/or powders of the invention.

A typical preferred liquid concentrate anthelmintic particularly suitable for water or aqueous dilution for use a deliverable drench composition or for lesser dilution for delivery as a pour on composition can have or include:

| A preference | Functionality | Quantity (w/w) |
|---|---|---|
| Abamectin | anthelmintic active | 1-20%<br>preferably from 2-8% |
| Glycerol formal | organic solvent | 4-85%<br>preferably from 20-85%<br>more preferably from 50-85% |
| xanthan gum | suspending agent, rheology modifier and/or gum | 0.1-20%<br>preferably below 5%<br>preferably from 5-20% |
| benzyl alcohol | anti-microbial agent/ co-solvent | 0-10%<br>preferably from 0.1-6% |
| Polysorbate 80 | surfactant/antifoam agent | 0-8%<br>preferably 0.1-5% |

Low gum formulations preferably are 5% w/w or below and high gum formulations about 5 to about 20% w/w.

The gum can be xanthan. Alginates of different viscosity grades may be used as well or instead.

Levamisole base may be added by the manufacturer or by the farmer prior to addition. Prior to use (i.e. at dilution) any suitable form of levamisole (e.g. levamisole base, levamisole HCl, etc) and any suitable BZ(s) can be added.

The formulation may contain a gum that can gel in water for formulations to be made up using water or it might contain thickeners that thicken in oil phase like Aerosil 200 or Thixcin R or a combination of both for formulations intended to be reconstituted interchangeably using water or oil.

Liquid content of the concentrate can be or include water miscible solvents (eg glycerol formal, propylene glycol, glycerine, etc). Non aqueous diluents(s) can be one or more of those or an oil.

Drench formulations are preferably given at 1 ml per 4 kg body weight or 1 ml per 5 kg body weight for sheep.

For cattle it is 1 ml per 10 kg body weight if a drench or 1 ml per 20 kg body weight if a pour on. Thus a need for higher active in the pour on deliverable composition.

All these are after dilution with water or a non-aqueous diluent.

Pour-on dose volume is preferably a maximum 1 ml/20 kg in current products.

For example about 50 to 70 ml of the concentrate might be needed to make up a litre of Abamectin drench. A greater 150 to 200 ml of the concentrate might be required to make 1 litre of pour on.

The ratios will vary depending upon the drug used.

An example as produced by the process of FIG. 7 is that of Example 0.

In FIG. 7 there is a high shear mixer used to provide a solution of glycerol formal ("GF"), benzyl alcohol ("BA"), Tween80™ and abamectin ("ABA"). To this is added a mix of the xanthan gum ("XG"), colloidal or fumed silicon dioxide ("silica"), and the antifoam agent ("A/foam").

This mixture of a solution/suspension leads to a storage stable liquid concentrate in the form of a suspension but with the ML active in solution.

4. Use of a Granule

In one embodiment the invention is a method of co-administration of anthelmintic actives to warm-blooded non-human animals which comprises
(A) preparing a delivery liquid composition containing
  (i) a diluent,
  (ii) a liquid or semisolid concentrate of an ML active, and
  (iii)(a) powdered and/or granulated materials) having an LEV active, (b) powdered and/or granulated material(s) having a BZ active, and/or (c) granulated material(s) having both an LEV active and a BZ active, said delivery liquid including, as a consequence of (ii) and/or a (iii) presence, sufficient suspending agent for at least one particulate active from (ii) and/or (iii) in the deliver liquid composition to ensure a disperse consistency, and
(B) administering such delivery liquid composition in a dosage amount to each said animal.

In one embodiment the invention is a method of treating an animal which comprises or includes, in any order (A (i) to A (iv)):
  (A) (i) providing or taking at least one volume of anthelmintic granules [preferably of substantial homogeneity] able to be associated (eg, by dispersion) with water or an aqueous composition or with a nonaqueous liquid or liquid system to provide a (preferably thixotropic or pseudoplastic) liquid composition containing one or more anthelmintic actives,
    (optionally (ii) providing or taking a liquid concentrate of at least one avermectin and/or at least one milbemycin),
    (iii) providing or taking a volume of water and/or an aqueous composition and/or nonaqueous liquid and/or liquid system, and
    (iv) providing or taking apparatus able to administer a (preferably thixotropic) liquid composition to such an animal; and
  (B) associating in any order (i) and (iii) or (i), (ii) and (iii), whether in the apparatus of A(iv) or not; and
  (C) using the apparatus of A(iv) to administer the (preferably thixotropic or pseudoplastic) aqueous and/or nonaqueous composition resulting from (B) to such an animal.

In one embodiment the invention is a method of orally treating an animal which comprises or includes, in any order (A (i) to A (iii)):
  (A) (i) providing or taking at least one volume of granules containing at least one beneficial agent able to be dispersed into water or an aqueous composition to provide a liquid dispersion of at least substantial homogeneity,
    (ii) providing or taking a volume of water and/or an aqueous composition, and
    (iii) providing or taking apparatus able to administer a thixotropic liquid composition to such an animal; and
  (B) associating in any order (i) and (ii), whether in the apparatus of A(iv) or not; and
  (C) using the apparatus of A(iii) to administer orally aqueous composition resulting from (B) to such an animal.

In one embodiment the invention is a method of administering a mix of anthelmintic actives to an animal which comprises
  (A) preparing an aqueous delivery composition
    (i) from a dry granular composition of at least one anthelmintic active, or
    (ii) from both a dry composition of at least one anthelmintic active and a liquid concentrate of at least one other anthelmintic active, and
  (B) administering an effective amount of the aqueous delivery composition to the animal.

In one embodiment the invention is a dosage system for orally dosing animals with at least one beneficial agent (preferably at least one anthelmintic active), said system requiring
(a) one or more packs of granules of the beneficial agent(s), and
(b)
  (ii) a drenching device and a mixing container, or
  (iii) a drenching device having a mixing reservoir,
when one or other, or both, (A) and/or (B) is in physical association with instructions whereby use of
the one or more packs
(A) a said mixing container or said mixing reservoir with water or a aqueous carrier and/or a nonaqueous liquid or liquid system as instructed in, and
(B) the drenching device for its fixed dosage amounts or a calibratable variable dosage amount,
(C) will deliver, in use, an effective amount of the beneficial agent(s) to each drenched target animal.

In one embodiment the invention is a dosage system for orally dosing animals with plural anthelmintic actives, said system comprising or including
(A) one or more packs of granules and/or granules and powder(s) of at least one anthelmintic active, and
(B) at least one container with an avermectin and/or milbemycin active in a liquid and/or semisolid concentrate form
(C)
  (i) a drenching device and a mixing container, or
  (ii) a drenching device having a mixing reservoir,
when one or more of (A), (B) and/or (C) is in physical association with instructions whereby use of
(a) all of one or more pack content(s),
(b) all of one or more container content(s),
(c) the mixing container or mixing reservoir with water or a aqueous carrier and/or a
(d) nonaqueous liquid or liquid system as instructed, and the drenching device for its fixed dosage amounts or its calibratable variable amount, will deliver, in use, an effective amount of the plural anthelmintic agents to each drenched target animal.

The granules offer an ability to hold in storage for farm/veterinary customization mixing/assessment of needs.

One or more packs and optionally one or more volumes of an ML liquid concentrate and/or other beneficial contents can be diluted into a drench gun for animal administration.

The present invention includes the use of dilutable powders, dilutable granules, and diluatable liquid concentrate(s) and/or semisolid concentrates to provide a multiactive anthelmintic formulation capable of oral, spray and/or purion delivery.

Preferably packs of granules or granules and powder(s) are emptied for dilution to a delivery system reservoir dilution to a delivery system reservoir volume. Likewise the liquid or semisolid concentrate(s).

As a kit packs and/or containers as modular amounts for combination or not would be provided of granules (single active, dual active, etc and optionally with trace elements and/or vitamins) and of a liquid concentrate of at least one ML (optionally with additives).

Preferably packs of granules or granules and powder(s) are emptied for dilution to a delivery system reservoir dilution to a delivery system reservoir volume. Likewise the liquid or semisolid concentrate(s).

In another aspect the invention is a drench gun (or like apparatus) dosing a delivery liquid composition as previously defined.

Analysis or experience can allow on farm customization of each mix at dilution for animal administration.

The invention will now be further described by way of the following non-limiting examples.

EXAMPLES

Example 1

Single Active Powder Formulations 1.1 Praziquantel

| Ingredient name | % (w/w) |
| --- | --- |
| Praziquantel | 38.7 |
| Aerosil 200 | 40.82 |
| SLS (solid) or Polysorbate 80 (liq) or other surfactant (solid or liq) | 20.4 (SLS) |

The fill weight is about 50 g/L of formulation. The adjuvant quantities may be optimized later. The delivery dose is 0.2 ml/kg (sheep).

In some embodiments minerals are additionally added.

Other adjuvants such as a buffer, suspending agents like xanthan gum, guar gum, or alginates may be added.

Wet granulation may be used using electrolyte solutions, buffers, and minerals, whereby the ingredients are sprayed on to the bulking agent.

Dual active formulations (e.g. including abamectin), may also include a wetting solution. The wetting agent can be a low or high liquid containing impregnated granule.

| Ingredient name | % (w/w) |
| --- | --- |
| Triclabendazole | 62.5 |
| Aerosil 200 | 25 |
| SLS (solid) or Polysorbate 80 (liq) or other surfactant | 12.5 (SLS) |

The fill weight is about 160 g/L of formulation.

A ball milling step may be used prior to the fluidized bed system for aggregate forming drugs.

In some embodiments if a liquid surfactant is used, such as polysorbate 80, the surfactant remains in the granules.

Granulation can be used to add potent drugs or beneficial agents (present below 5%) or in general to incorporate very dense (i.e. denser than 1 bulk density) materials (formulation ingredients) like metal salts where there is a perceived risk of segregation either in the granules or in the reconstituted product. Granulation will also be used if a flow problem is perceived in general or if the formulation tends to lump on storage (making it non user friendly or may cause difficulty during reconstitution).

Example 2

Dual Active Powder Formulations (Low Surfactant)

2.1 Levamisole and Albendazole

| Ingredient name | % (w/w) |
| --- | --- |
| Levamisole HCl | 35.4 |
| Albendazole | 22.12 |
| Cobalt EDTA | 15.93 |

-continued

| Ingredient name | % (w/w) |
|---|---|
| Aerosil 200 | 17.7 |
| SLS (Solid) or Polysorbate 80 (Liq) or other surfactant (may be liq or solid) | 8.8 (SLS) |

The composition is reconstituted at 117 g/L and administered at 0.2 ml/kg.

In some embodiments a mineral can be added along with other adjuvants like buffers or suspending agents like xanthan gum, guar gum, and alginates.

2.2 Levamisole and Praziquantal

| Ingredient name | % (w/w) |
|---|---|
| Levamisole HCl | 37.4 |
| Praziquantel | 17.75 |
| Cobalt EDTA | 16.8 |
| Aerosil 200 | 18.7 |
| SLS (Solid) or Polysorbate 80 (Liq) or other surfactant (Liq or Solid) | 9.35 (SLS) |

The composition is reconstituted at 107 g/L and administered at 0.2 ml/kg.

2.3 Levamisole and Triclabendazole

| Ingredient name | % (w/w) |
|---|---|
| Levamisole HCl | 29 |
| Triclabendazole | 36.23 |
| Cobalt EDTA | 13.04 |
| Aerosil 200 | 14.4 |
| SLS (Solid) or Polysorbate 80 (Liq) or other surfactant | 7.2 (SLS) |

The composition is reconstituted at 138 g/L.

Example 3

Dual Active Granule Formulations (Low Surfactant)

3.1 Levamisole and Albendazole

| Ingredient name | % (w/w) |
|---|---|
| Levamisole HCl | 43.20 |
| Albendazole | 27.42 |
| Cobalt EDTA | 19.2 |
| Xanthan Gum | 3.3 |
| Polysorbate 80 (Other surfactant) | 1.6 |
| Sodium selenate | 1.32 |
| Citric Acid | 3.3 |
| NaOH | 0.625 |
| Abamectin | — |
| Benzyl Alcohol | — |
| Colloidal Silicon dioxide | — |

The composition is reconstituted at 91 g/L and administered at 0.2 ml/Kg.

Figure 2:
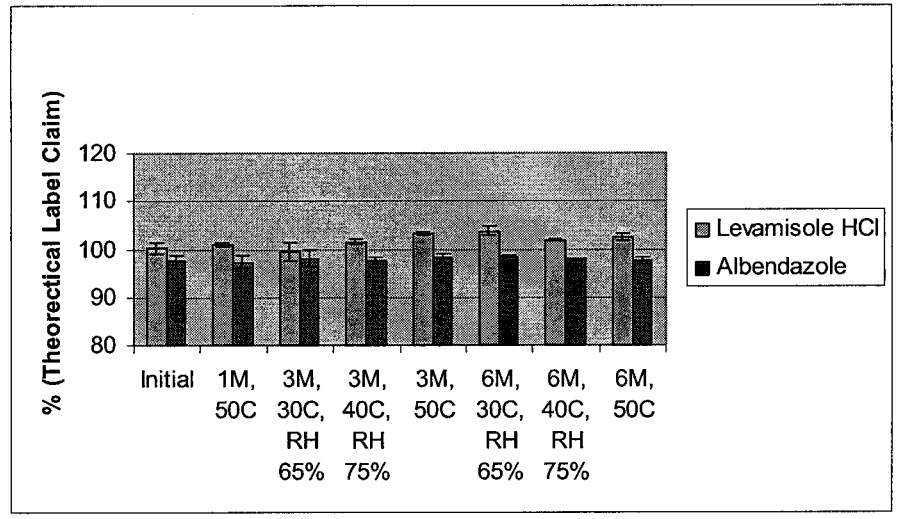
FIG. 2 shows stability of the Example 6 formulation over time in months (M) and the temperatures shown in (c).

This formulation is a dual active formulation comprising a low surfactant polysorbate 80 (below 10% is less), a mineral (sodium selenate), and a bulk mineral (cobalt EDTA). In some embodiments a preservative can also be added. The stability of this formulation is shown in FIG. 2.

In some embodiments ball milling is used prior to charging in to the fluidized bed system, such as aggregate forming drugs (e.g. albendazole).

3.2 Levamisole and Oxfendazole

| Ingredient name | % (w/w) |
|---|---|
| Levamisole HCl | 46.65 |
| Oxfendazole | 26.42 |
| Cobalt EDTA | 20.4 |
| Xanthan Gum | 1.2 |
| Polysorbate 80 (Other surfactant) | 3 |
| Sodium selenate | 1.4 |
| Citric Acid | 0.9 |
| NaOH | 0.2 |
| Abamectin | — |
| Benzyl Alcohol | — |
| Colloidal Silicon dioxide | — |

Figure 3:
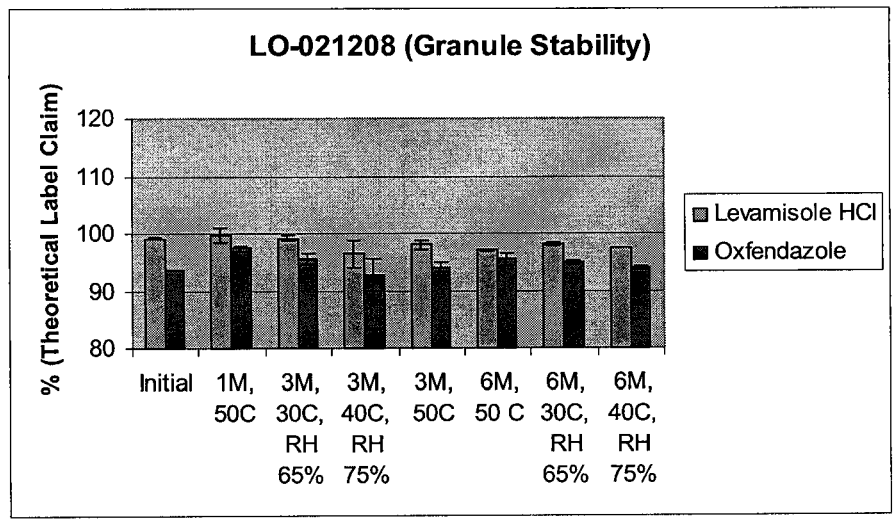
FIG. 3 shows the stability of a concentrate as in Example 7 in a typical package being by way of example aluminium foil (but it could be a plastic sachet), bottle eg. HOPE or other)

The composition is reconstituted at 171.5 g/L. The same comments made for 3.2 apply. The stability data for this composition is shown in FIG. 3.

Example 4

Dual Active Granule Formulation (High Surfactant)

4.1 Levamisole and Oxfendazole

| Function | Excipient Class (% Dry Wt) | Ingredient |
|---|---|---|
| Actives | Drugs Total (57.5%) | Levamisole HCl (36.7%) & oxfendazole (20.8) |
| Suspending Agent Rheology Modifier | Gum (1.4%) | Xanthan Gum |
| Anti-microbial preservative | Preservative (2.8%) | Benzyl Alcohol* |
| Wetting Agent | Surfactant (13.8%) | Polysorbate 80 |
| pH Stabilizer | Buffer (1.6%) | Citric Acid & NaOH |
| Adsorbent, Flow modifier, Bulking Agt; Gum & Drug Dispersant; Disintegrating Agt | Bulking Agent (5.7%) | Colloidal SiO$_2$ |
| Mineral Supplements | Minerals (17.2%) | Cobalt EDTA & Na Selenate |

The composition is reconstituted at 220 g/L to L) and administered at 0.1 ml/Kg. This formulation exhibits good stability (e.g. as for the triple high surfactant example).

This formulation is a dual active formulation utilising the high surfactant polysorbate 80 (above 10% is high), a potent mineral (sodium selenate) and a bulky mineral (Cobalt EDTA). This can be used as a dual standalone.

In some embodiments ball milling is used prior to charging in to the fluidized bed system, such as aggregate forming drugs (e.g. albendazole).

In-Use Suspendability

The concentration of the reconstituted granule in water was 1.1 kg/5 L. Oxfendazole was chosen as a marker compound for drug suspension stability.

(Levamisole Fully Soluble)

Initial: 100 mg/g 2 h: At the top was 96 mg/g and at the bottom was 105.2 mg/g 4 h: At the top was 98 mg/g and at the bottom was 99 mg/g 4 days: At the top was 95.7 mg/g and at the bottom was 98 mg/g These results demonstrated that the reconstituted suspension is physically stable up to 4 days.

In-Use Stability—Physico-Chemical

The stability of reconstituted drug product was investigated after storage at 30 and 40° C. for 1 month. It was found that there was no chemical degradation of the benzimidazole and less than 2% degradation of Levamisole. It was additionally found that there was no significant change in the pH or viscosity of the reconstituted granule formulation.

In-Use Flow Testing

Using a standard drench gun it was found that the in-use flow testing was excellent.

The dual and triple active granule formulations are thixotropic (shear thinning) with a viscosity of 500-900 cP at 20° C.

Little change was observed when the formulation was combined with a liquid concentrate of an ML active.

Example 5

Triple Active Granule Formulations (Low Surfactant)

In the low surfactant methods abamectin is first micronized, precipitated and then reconstituted and sprayed.

5.1 Levamisole, Oxfendazole

| Ingredient name | % (w/w) |
| --- | --- |
| Levamisole HCl | 45.82 |
| Oxfendazole | 25.95 |
| Cobalt EDTA | 20 |
| Xanthan Gum | 1.43 |
| Polysorbate 80 (Other surfactant) | 2.9 |
| Antifoam AF Emulsion | 0.3 |
| Sodium selenate | 1.4 |
| Citric Acid | 0.9 |
| NaOH | 0.16 |
| Abamectin ** | — |
| Benzyl Alcohol | — |
| Colloidal Silicon dioxide | — |

Figure 4:
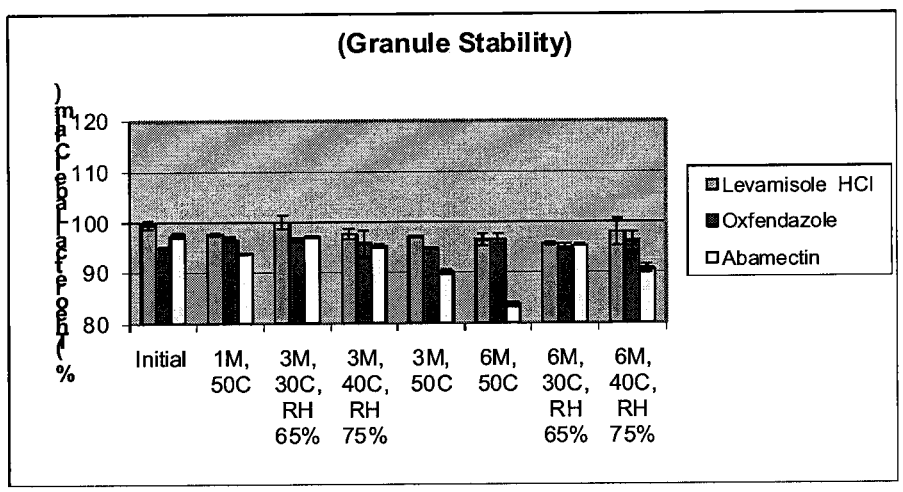
FIG. 4 shows the stability of a concentrate as in Example 9.

The composition is reconstituted at a concentration of 175 g/L. The stability is shown in FIG. 4.

5.2 Levamisole, Albendazole

| Ingredient name | % (w/w) |
| --- | --- |
| Levamisole HCl | 42.4 |
| Albendazole | 26.51 |
| Cobalt EDTA | 18.6 |
| Xanthan Gum | 3.2 |
| Polysorbate 80 (Other surfactant) | 2.65 |
| Antifoam AF Emulsion | 0.53 |
| Sodium selenate | 1.27 |
| Citric Acid | 3.2 |
| NaOH | 0.6 |
| Abamectin ** | — |
| Benzyl Alcohol | — |
| Colloidal Silicon dioxide | — |

Figure 5:
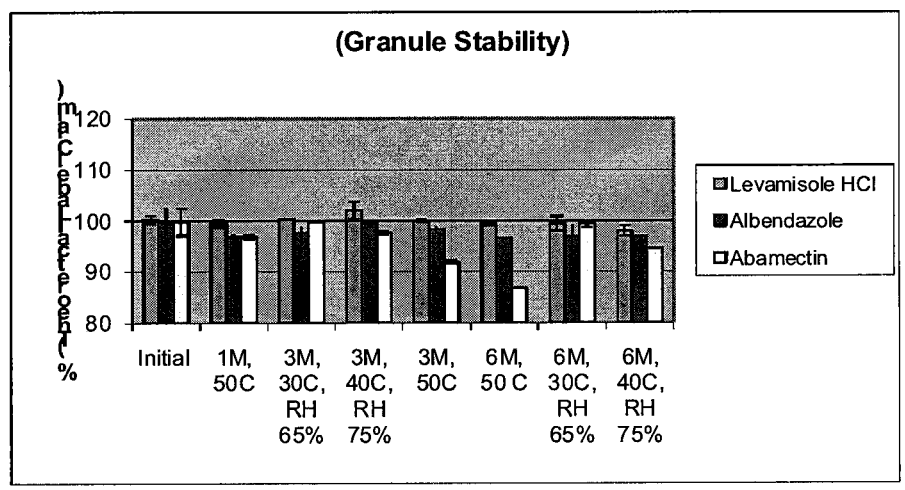
FIG. 5 shows the stability of a concentrate as in Example 10.

The composition is reconstituted at 94 g/L and administered at 0.2 ml/Kg. The stability is shown in FIG. 5.

Example 6

Triple Active Granule Formulations (High Surfactant)

In the high surfactant methods abamectin is incorporated as a fine dispersion after dispersal in benzyl alcohol.

6.1 Levamisole, Oxfendazole and Abamectin

| Ingredient name | % (w/w) |
| --- | --- |
| Levamisole HCl | 35.42 |
| Oxfendazole | 20 |
| Cobalt EDTA | 15.5 |
| Xanthan Gum | 1.77 |
| Polysorbate 80 (Other surfactant) | 15.5 |
| Antifoam AF Emulsion | — |
| Sodium selenate | 1.06 |
| Citric Acid | 1.32 |
| NaOH | 0.25 |
| Abamectin (microfine) | 0.93 |
| Benzyl Alcohol | 2.66 |
| Colloidal Silicon dioxide | 5.53 |

The abamectin was first dissolved in glyceryl formal and polysorbate 80 mixture (Glyceryl formal 88% and polysorbate 80 3.6%). The percentage indicates the composition ratio used, and is not related to the formulation. The abamectin is then precipitated out in water under agitation (Silverson).

The fine precipitated abamectin is obtained from the dispersion by centrifuging (4200 rpm for 5 min) the dispersion after decanting the supernatant layer (i.e. glyceryl formal and polysorbate 80 is removed during centrifuging followed by decanting). The microfine abamectin was then reconstituted quantitatively using wetting solution made up of water and polysorbate 80.

It is envisaged that the stability of labile drugs will be further improved if separate granulation of actives occurs. For example, the contents in a sachet may be a mixture of two granules to prevent intimate contact of the labile drugs. In some embodiments the granules may be packed in two separate sachet packs.

Figure 6:
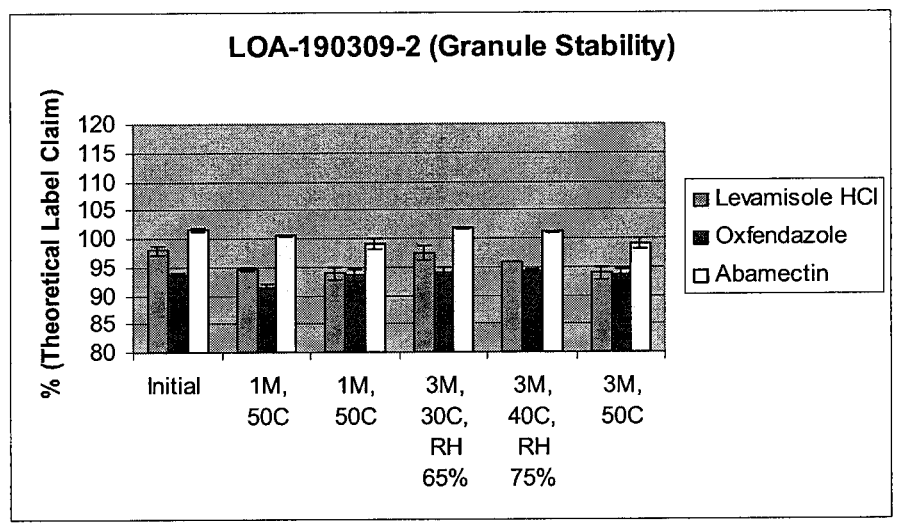
FIG. 6 shows the stability of a concentrate of Example 11.

The composition is reconstituted at 175 g/L and administered at 0.1 ml/Kg. The stability is shown in FIG. 6.

Chemical and Physical Stability—Abamectin

When reconstituted with water, the sstability of abamectin in the reconstituted triple active formulation was investigated after storage at 30 and 40° C. for 1 month. It was observed that abamectin had less than 2% degradation and there was no physical change in pH or viscosity.

In-Use Flow Testing—Reconstituted Drug Products

Using a standard drench gun it was found that the in-use flow testing was excellent.

The dual and triple active granule formulations are thixotropic (shear thinning) with a viscosity of 500-900 cP at 20° C.

Example 7

Triple Active Granule Manufacture

A triple active granule was prepared in accordance with the table below.

| Name of ingredient | Qty per L (g) | Qty % (w/w) |
| --- | --- | --- |
| Levamisole HCL | 80 | 36.4 |
| Oxfendazole | 45.3 | 20.6 |
| Cobalt EDTA | 35 | 15.9 |
| Sodium Selenate | 2.4 | 1.09 |
| Abamectin | 2.1 | 0.96 |
| Xanthan Gum | 3 | 1.36 |
| Colloidal Silicon Dioxide | 12.5 | 5.69 |
| Polysorbate 80 | 30 | 13.64 |
| Benzyl Alcohol | 6 | 2.73 |
| Citric Acid | 3 | 1.36 |
| Sodium Hydroxide | 0.57 | 0.26 |

-continued

| Name of ingredient | Qty per L (g) | Qty % (w/w) |
|---|---|---|
| Water (1) | 76.2-114.3 (for ABA) | — |
| Water (2) | 25-42 ml (for mineral) | — |
| Water (3) | 2-3 ml (to flush lines) | — |
| TOTAL | 219.87 | 100% |

The manufacturing process for the triple granule comprises the steps of:
1. dry mixing levamisole HCL, cobalt EDTA and xanthan gum,
2. mixing oxfendazole and the aerosil in a polybag and passing it through a 0.8-1 mm sieve,
3. dissolving the abamectin in benzyl alcohol and adding polysorbate 80 to it while under agitation,
4. adding water to the abamectin while under agitation until a hazy white colored dispersion is produced which is free from particulates (particulates which are observed visually),
5. loading the powders from steps 1 and 2 into the FBP bowl and mixing for five minutes,
6. spraying the step 3 dispersion,
7. prepare a solution of citric acid, sodium hydroxide and sodium selenate in water,
8. spraying the step 7 solution and keeping the fluidized bed warm (40-55° C.), and
9. drying the granules till the moisture content of 2-3% is achieved (KF method).

The granule produced by this method had good stability and dispersed well in water.

Example 8

Triple Active Granule Efficacy Study

A triple active granule was prepared in accordance with the table below.

| Raw Material | Percentage | Batch |
|---|---|---|
| Levamisole Hydrochloride | 35.071% w/w | 526.06 g |
| Oxfendazole | 19.859% w/w | 297.88 g |
| Abamectin 95% | 0.969% w/w | 14.54 g |
| Cobalt EDTA | 15.343% w/w | 230.15 g |
| Sodium Selenate | 1.052% w/w | 15.78 g |
| Xanthan Gum | 1.973% w/w | 29.59 g |
| Colloidal Silicone Dioxide 200 (CSD) | 8.386% w/w | 125.79 g |
| Benzyl Alcohol | 2.630% w/w | 39.45 g |
| Polysorbate 80 | 13.152% w/w | 197.27 g |
| Distilled Water | (0-35% w/w) | (0-700 g) |
| Citric Acid Anhydrous | 1.315% w/w | 19.73 g |
| Sodium Hydroxide | 0.250% w/w | 3.75 g |
| Distilled Water | (14.667% w/w) | (220 g) |
| Total | 100% w/w | 1,499.99 g |

The granules were produced using the following process:
1. sodium selenate was dissolved in purified water, citric acid anhydrous and sodium hydroxide were added to the solution and mixed well to produce the Se solution,
2. abamectin was dissolved in benzyl alcohol, polysorbate 80 was added to the solution and mixed well, and then a variable quantity of water (0-700 g) was added to the solution and mixed well to produce the ABA solution,
3. levamisole HCL, cobalt EDTA and xanthan gum were passed through a 40-mesh screen and mixed,
4. oxfendazole and colloidal silicon dioxide 200 were passed through a 40-mesh screen and mixed,
5. the powder mixtures of (3) and (4) were placed in glatt granulator/dryer insert,
6. the powder mixtures of (5) were fluidized and warmed up,
7. the ABA solution was sprayed onto the powder mixtures at a variable spray rate (20-40 g/minute) with a variable inlet air temperature (30-60° C.) with suitable fluidising,
8. the Se solution was sprayed onto the powder mixtures with a spray rate of 15 g/minute and an inlet air temperature of 50° C. with suitable fluidising,
9. the granule formed was dried with an inlet air temperature of 50° C. until the product temperature reached 50° C.,
10. the granule was cooled to 25° C.,
11. the dried granule was passed through a 18-mesh (850 μm) sieve, grinding up any lumps too big to pass through,
12. the granule was tested for Loss on Drying (LoD), Mean Particle Diameter (MPD) and density (bulk and tapped).

8.1 Stability Study

The study was conducted to review the quantity of spray solution, spray rate and inlet air temperature. Statistical analysis of the response data including flow-ability, dispersing-ability in water and sedimentation speed will be used to identify the optimal level of quantity of spray solution, spray rate and inlet air temperature.

The quantity of spray solution (0, 350, 700 g), spray rate (20-40 g/min) and inlet air temperature (30-60° C.) was varied in an attempt to understand the effect of changing these variables, individually and in combination, to identify an optimal combination of quantity of spray solution and process parameters to produce suitable granule.

8.2 Efficacy Study

A cross-over study was performed to determine the blood plasma concentrations of abamectin, oxfendazole and levamisole following oral treatment with reconstituted granule product containing these three anthelmintics. The efficacy of the reconstituted triple granule was compared to Matrix Hi Mineral Oral Drench for Sheep.

Eight female romney sheep of similar age and body weight were used. The criteria for selection was to include animals that had not been dosed with a persistent anthelmintic formulation within 6 months of selection for the trial. Persistent anthelmintics include slow release capsules (e.g. Bionic), injectable or oral forms of moxidectin and closantel. Sheep were acclimated to the study site for 14 days before treatment.

Each sheep was randomly assigned to the treatment group and received one treatment and then the alternate treatment 21 days later.

The study procedures were as follows:
sheep were weighed using calibrated scales on Day −1 for weight ranking and allocation to treatment groups. They were weighed again on Day 20, with the treatment doses calculated from the Day −1 or Day 20 weights respectively.

Triple-Active Granules were reconstituted in the laboratory on Day −1 and Day 20, the day immediately before the treatment days. Granules were weighed and added with the calculated volume of water to a 2 litre schott bottle and inverted a number of times until the granules were wetted and fully dispersed. On the morning of treatment the schott bottle was again gently inverted 3 or 4 times to ensure a homogeneous mix and approximately 100 mL was decanted from which the syringe was filled for dosing.

Treatments were administered on Day 0 and Day 21 at a dose volume of 1 ml/5 kg. Dosing was done using a 12 mL graduated syringe. Dose volume and time of administration was recorded and checked for each sheep.

Blood samples were collected before treatment, and after treatment at 0.5, 1, 2, 6, 8, 12, 15, 24 and 36 hrs. Samples were assayed for abamectin, oxfendazole and levamisole, or their metabolites.

Samples of both the reconstituted triple-active granule liquid and the Matrix Hi Mineral positive control product as used for the treatments, were assayed for abamectin, oxfendazole and/or levamisole.

Results

First Treatment Day

Treatment 1

Reconstituted combination granule

Assay: abamectin, 1.06 g/L, oxfendazole 22.63 g/L, levamisole HCL 40.87

Treatment 2

Positive control "Matrix Hi Mineral Oral Drench for Sheep"

Assay: abamectin, 1.08 g/L, oxfendazole 23.7 g/L, levamisole HCL 2.187 g/L.

Second Treatment Say

Treatment 1

Reconstituted combination granule

Assay: abamectin, 1.04 g/L, oxfendazole 22.40 g/L, levamisole HCL 40.60

Treatment 2

Positive control "Matrix Hi Mineral Oral Drench for Sheep"

Assay: abamectin, 1.08 g/L, oxfendazole 23.69 g/L, levamisole HCL 42.45

The table below shows the results from the blood samples with the pooled mean data for the 8 sheep for each treatment (combined for both phases of the cross-over study). Oxfendazole plasma levels are presented as two separate plasma metabolites: oxfendazole and fenbendazole, and the total of these two expressed as "total-oxfendazole". All plasma metabolite units are presented as mg/kg

| Comparison | Treatment | $C_{max}$ | $T_{max}$ |
|---|---|---|---|
| abamectin comparison | abamectin | 0.017 | 24 hrs |
|  | Matrix Hi Mineral | 0.017 | 24 hrs |
| levamisole comparison | levamisole | 1.445 | 1 hr |
|  | Matrix Hi Mineral | 1.405 | 2 hr |
| oxfendazole comparison | oxfendazole | 0.792 | 15 hrs |
|  | Matrix Hi Mineral | 0.845 | 8 hrs |
| fenbendazole comparison | fenbendazole | 0.209 | 12 hrs |
|  | Matrix Hi Mineral | 0.189 | 24 hrs |
| total oxfendazole comparison | oxfendazole | 0.984 | 12 hrs |
|  | Matrix Hi Mineral | 0.987 | 8 hrs |

This table shows that . . .

Example 9

Single Active Liquid Concentrate

Shown below is a liquid concentrate formulation suitable for aqueous dilution.

| Function | Excipient (% w/w) | Ingredient |
|---|---|---|
| Single Active | Drug (4.5%) | Abamectin |
| Solubilizer & Stabilizer | Solvent (82.3%) | Glyceryl Formal |
| Suspending Agent Rheology Modifier | Gum (5.8%) | Xanthan Gum |
| Anti-Microbial Agent: co-Solvent | Preservative (3.9%) | Benzyl Alcohol |
| Wetting Agent Dispersing agent (prevents aggregation on reconstitution) | Surfactant (1.9%) | Polysorbate 80 |
| Bulking Agent Gum & Drug Dispersant Anti-caking Agent | Bulking Agent (0.6%) | Colloidal $SiO_2$ |
| Prevents foam on reconstitution | Antifoam Agent (1%) | Antifoam AF |

Colloidal SiOz can be present in even greater amounts as a viscosity builder.

In some embodiments the forumulation includes antifreeze, chelating agents, stabilizers, or a penetrant enhances. If a penetrant enhancer is used, then preferably it is for pour on use post dilution. Preferably any such addition use is less than 5% w/w.

Other surfactants (e.g. cationic, anionic or non ionics), gums, buffering systems may be added. The choice of surfactant will depend on drug properties and the medium used to reconstitute the concentrate. Solvents like propylene glycol may be added as cosolvents or solvents replacing glycerol formal. Propylene glycol may also behave as antifreeze or help in preparation of microemulsions (that are clear looking abamectin or other chemically similar drugs in water).

If colloidal silicon dioxide higher than say 2-3% is used, it not only acts as a anticaking agent but also as a bulking agent/adsorbing agent (for uniform distribution of potent ingredients or as a viscolytic agent for organic based formulations).

It is envisaged that it is diluted with water, an aqueous composition or a non-aqueous liquid or composition, for example, a pour on type concentrate (which will form water based pour ons upon reconstitution). The final product is administered at 1 ml/kg. For example, about 150 or 200 ml is required to make up a litre of pour on with high gum/abamectin concentrate. This volume will vary depending upon the drug used in addition to the ML anthelmintic.

For example, for levamisole mase (used in a pour on concentrate owing to its penetration properties) about 600 to about 700 ml/L for 200 g of base). Levamisole base (200 g) needs glyceryl formal (200 g); Polysorbate 80 (about 400 g) to microemulsify the base.

Stability Trial Post Mix

The stability of the reconstituted abamectin was investigated after storage at 20-25° C. for 4 days. It was observed that there was no degradation of the abamectin and some degradation of the benzyl alcohol to aldehyde. The reconstituted formulation remained suspended with no settling

Example 10

Single Active Oil-Based Liquid Concentrate

An oil based liquid concentrate formulation example suitable for water or oil dilution:

| Ingredient | Function | w/w |
|---|---|---|
| Abamectin | active | 10.3%, |
| Xanthan Gum | suspending agent | |
| Thixcin R | protective colloid | |
| Aerosil 200 or R 972 | rheology modifier | |
| Benzyl Alcohol | | |
| Anti-Microbial Agent | | 67% |
| Solvent | | |
| Particle size modifier | If in water based reconstitution | |
| Propylene Glycol (optional) | Solvent - especially if water is used for reconstitution) | |
| Polysorbate 80 | Wetting agent - dispersing agent as prevents aggregation of drug | 22.45%, |
| Colloidal silicon dioxide | Anticaking agent - needed if xanthan is used as a thickener. If aerosil is used as a thickener may not use it again as an anticaking agent. | 0.6%, |
| Antifoam Agent (optional) | May be an emulsion or free flowing powder | |

The formulation should be diluted to 12-15 ml/L. The concentration of the abamectin may be reduced to below 5% w/w if needed by increasing the quantity of benzyl alcohol and polysorbate in the above ratio.

Other surfactants (cationic, anionic or non ionics), gums, buffering systems may be added.

Figure 9:
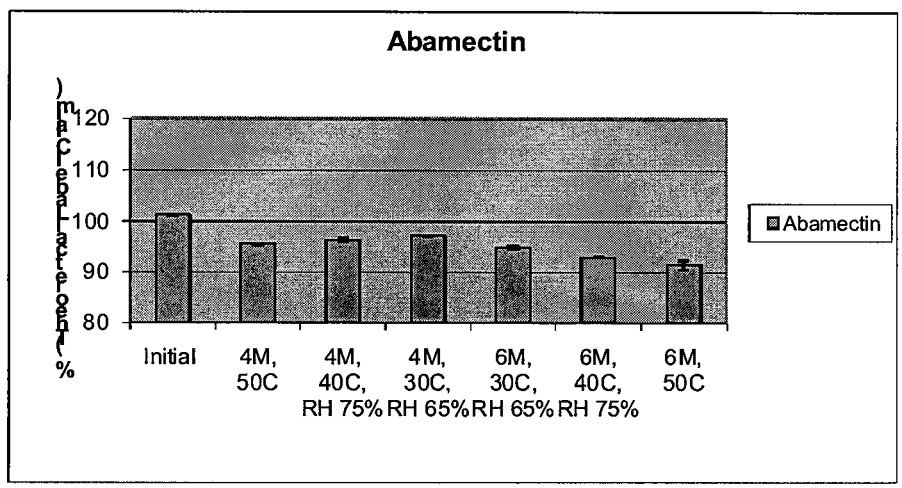
FIG. 9 shows the stability of a concentrate as in Example 13 in a typical container.

The stability is shown in FIG. 9.

Whilst the liquid concentrate is preferably in a container such as a bottle (glass or plastic) in some aspects the concentrate can be in capsules (e.g. hard or soft gelatine—with or without drug or flavor enhancing agents). This is particularly so if any added beneficial agent is malodorous. If for example in that form they can be still diluted prior to administration or be administered as is.

Suitable applicators for administering and of the delivery composition are those available from N J Phillips Pty Limited, Instrument Supplies Ltd, Simcrotech Ltd and PrimaTech Ltd. Particularly preferred are backpack reservoired applicators of N J Phillips Pty Limited (e.g. with 2.5 litre backpack) and a variable dose capability.

The invention is further described by the following numbered paragraphs:

1. An anthelmintic composition in the form of a stable granule comprising two or more anthelmintic actives selected from one or more imidazothiazoles, one or more benzimidazoles, one or more macrocyclic lactones, one or more salicylanilides, praziquantel, the stable granule being readily dispersible in water to provide a homogenous mixture of the anthelmintic actives for administration to a non-human mammal,
the granule further comprising a suspending agent if the anthelmintic actives comprise a benzimidazole, a wetting agent if the anthelmintic actives comprise a macrocyclic lactone, a wetting agent if the anthelmintic actives comprise a salicylanilide and a suspending agent if the anthelmintic actives comprise praziquantel.
2. A composition of paragraph 1 comprising levamisole HCL and a macrocyclic lactone.
3. A composition of paragraph 1 comprising levamisole HCL and a benzimidazole.
4. A composition of paragraph 1 comprising levamisole HCL, a benzimidazole and a macrocyclic lactone.
5. A composition of paragraph 1 comprising a benzimidazole and a macrocyclic lactone.
6. A composition of paragraph 1 comprising praziquantel and one or more anthelmintic actives selected from one or more imidazothiazoles, one or more benzimidazoles, one or more macrocyclic lactones, one or more imidazothiazoles
7. A composition of any one of paragraphs 1 to 6 wherein the macrocyclic lactone is selected from avermectin, ivermectin and abamectin.
8. A composition of any one of paragraphs 1 to 6 wherein the benzimidazole is selected from oxfendazole, albendazole or fenbendazole.
9. A composition of any one or more of paragraphs 1 to 8 comprising a particulate source of one or more minerals.
10. A composition of any one or more of paragraphs 1 to 9 wherein the granules comprise a suspending agent or rheology modifier.
11. A composition of paragraph 10 wherein the suspending agent or rheology modifier is a gum.
12. A composition of any one or more of paragraphs 1 to 11 wherein the granules comprise an anionic surfactant or wetting agent.
13. A composition of paragraph 12 wherein the wetting agent is polysorbate 80.
14. A composition of any one of paragraphs 1 to 13 wherein the granules comprise a dispersant.
15. A composition of paragraph 14 wherein the dispersant is colloidal silicon dioxide.
16. A composition of any one or more of paragraphs 1 to 15 wherein the granules comprise about 30, 35, 40, 45, 50, 55, 60, 65 or 70% w/w of the anthelmintic actives.
17. A composition of any one or more of paragraph 1 to 16 wherein the granule comprises less than 3, 2, or 1% w/w water.
18. A composition of any one of paragraphs 1 to 17 wherein the granules are free of pyrrolidones.
19. A composition of any one of paragraphs 3 to 18 comprising
from about 1 to about 40% w/w benzimidazole,
optionally a suspending agent, and
from about 1 to about 70% w/w levamisole HCL.
20. A composition of paragraph 19 comprising 1, 5, 10, 15, 20, 25, 30, 35 or 40% w/w macrocyclic lactone.
21. A composition of any one of paragraphs 1 to 20 wherein the granules comprise one or more of
a particulate thixotrope,
a particulate rheology modifier
a suspending agent,
a wetting agent, and
a anti-colloidal,
or any combination of any two or more thereof.
22. A dosage system for orally dosing animals with an anthelmintic agent, the system comprising
(a) one or more packs of granules for addition into an aqueous liquid, the granules comprising
(i) a benzimidazole and a suspending agent for the benzimidazole,
(ii) a macrocyclic lactone and a wetting agent,
(iii) a salicylanilide and a wetting agent,
(iv) praziquantel and a wetting agent,
(v) an imidazothiazole and one or more anthelmintic agents selected from benzimidazoles, macrocyclic lactones, salicylanilides, and praziquantel, and optionally a suspending agent, (b) a suspending agent if (i) the granules do not comprise a suspending agent, or (ii) additional suspending agent is required to suspend the anthelmintic actives in the liquid.

23. A dosage system of paragraph 22 further comprising (i) a drenching device and a mixing container, or (ii) a drenching device having a mixing reservoir, when in use the one or more packs are used with a mixing container or mixing reservoir with water or an aqueous carrier or a drenching device for its fixed dosage amounts or a calibrated variable dosage amount to deliver an effective amount of the anthelmintic actives to an animal.

24. A dosage system of paragraph 22 or 23 wherein the granules contain a suspending agent.

25. A dosage system of paragraph 24 wherein suspending agent is added to the liquid.

26. A dosage system of paragraph 22 to 25 wherein the suspending agent is a gum.

27. A dosage system of paragraph 22 to 26 wherein the suspending agent of (a)(i) is a non-colloidal agent.

28. A dosage system of paragraph 27 wherein the non-colloidal agent is silicon dioxide.

29. A dosage system of any one of paragraphs 22 to 28 wherein the liquid is water.

30. A dosage system of any one of paragraphs 22 to 28 wherein the liquid is an anthelmintic concentrate.

31. A dosage system of any one of paragraphs 22 to 28 wherein the liquid contains ivermectin, avermectin and/or milbemycin in a liquid concentrate form.

32. A dosage system of any one of paragraphs 22 to 31 wherein the liquid is suitable for administration to animals for up to one month after mixing.

33. A dosage system of any one of paragraphs 22 to 32 wherein the granules comprise
    from about 10 to about 40% w/w benzimidazole, and
    from about 10 to about 60% w/w levamisole HCL.

34. A dosage system of any one of paragraphs 22 to 33 wherein the granules comprise 15, 20, 25, 30, 35 or 40% w/w macrocyclic lactone.

35. A dosage system of any one of paragraphs 22 to 34 wherein the granules comprise a particulate source of one or more minerals.

36. A dosage system of any one of paragraphs 22 to 35 wherein the granules comprise about 30, 35, 40, 45, 50, 55, 60, 65 or 70% w/w anthelmintic actives.

37. A dosage system of any one of paragraphs 22 to 36 comprising 2, 3, 4, 5 or six anthelmintics 38. A dosage system of any one of paragraphs 22 to 36 comprising a benzimidazole, levamisole and a macrocyclic lactone.

39. A method of preparing a stable liquid delivery formulation for treating an animal comprising the steps of
(a) providing one or more packs of granules, the granules comprising
(i) a benzimidazole and a suspending agent for the benzimidazole,
(ii) a macrocylic lactone and a wetting agent,
(iii) a salicylanilide and a wetting agent,
(iv) praziquantel and a wetting agent,
(v) an imidazothiazole and one or more anthelmintic agents selected from benzimidazoles, macrocylic lactones, salicylanilides, and praziquantel, and optionally a suspending agent,
(b) adding the granules from the one or more packs of granules to an aqueous liquid,
(c) adding a suspending agent if (i) the granules do not comprise a suspending agent, or (ii) additional suspending agent is required to suspend the anthelmintic actives in the liquid.

40. A method of paragraph 39 wherein the granules contain a suspending agent.

41. A method of paragraph 39 or 40 wherein a suspending agent is added to the aqueous liquid.

42. A method of any one of paragraphs 39 to 41 wherein the suspending agent is a gum.

43. A method of any one of paragraphs 39 to 42 wherein the suspending agent of (a)(i) is a non-colloidal agent.

44. A method of paragraph 43 wherein the non-colloidal agent is silicon dioxide.

45. A method of any one of paragraphs 39 to 44 wherein the aqueous liquid is water.

46. A method of any one of paragraphs 39 to 45 wherein the aqueous liquid is an anthelmintic concentrate.

47. A method of any one of paragraphs 39 to 46 wherein the aqueous liquid contains avermectin and/or Milbemycin in a liquid concentrate form.

48. A method of any one of paragraphs 39 to 47 wherein the liquid delivery formulation is suitable for administration to animals for up to one month after mixing.

49. A method of any one of paragraphs 39 to 48 wherein the mixing of the granules with the aqueous liquid is performed at, or near, the site of animal administration.

50. The method of any one of paragraphs 39 to 49 further comprising a step before the providing step of determining the treatment needs of one or more animals.

51. The method of any one of paragraphs 39 to 50 further comprising administering the liquid to one or more animals.

52. A method of any one of paragraphs 39 to 51 wherein the granules comprise
    from about 10 to about 40% w/w benzimidazole, and
    from about 10 to about 60% w/w levamisole HCL.

53. A method of any one of paragraphs 39 to 52 wherein the granules comprise 15, 20, 25, 30, 35 or 40% w/w macrocyclic lactone.

54. A method of any one of paragraphs 39 to 53 wherein the granules comprise a particulate source of one or more minerals.

55. A method of any one of paragraphs 39 to 54 wherein the granules comprises a suspending agent.

56. A method of any one of paragraphs 39 to 55 wherein the granules comprise a gum.

57. A method of any one of paragraphs 39 to 56 wherein the granules comprise an anionic surfactant.

58. A method of any one of paragraphs 17 to 52 wherein the granules comprise about 30, 35, 40, 45, 50, 55, 60, 65 or 70% w/w of the anthelmintic agents.

59. A method of forming an anthelmintic composition comprising the steps of: providing two or more anthelmintic actives selected from one or more imidazothiazoles, one or more benzimidazoles, one or more macrocyclic lactones, and praziquantel,
providing a suspending agent if the anthelmintic actives comprise a macrocyclic lactone, providing a wetting agent if the anthelmintic actives comprises a benzimidazole, mixing the macrocylic lactone with the suspending agent if a macrocylic lactone is present,
mixing the benzimidazole with the wetting agent if a benzimidazole is present, combining the anthelmintic actives, and
granulating the anthelmintic actives.

60. A method of paragraph 59 wherein a stabilising agent is combined with the anthelmintic actives prior to granulation.

61. A method of paragraph 59 wherein the stabilising agent is a gum.
62. A method of any one of paragraphs 59 to 61 wherein the granules further comprise a particulate source of one or more minerals.
63. A method of any one of paragraphs 59 to 62 wherein the granules comprise a suspending agent or rheology modifier.
64. A method of paragraph 63 wherein the suspending agent or rheology modifier is a gum.
65. A method of any one of paragraphs 59 to 64 wherein the granules comprise an anionic surfactant or wetting agent.
66. A method of paragraph 65 wherein the wetting agent is polysorbate 80.
67. A method of any one of paragraphs 59 to 66 wherein the granules comprise a dispersant.
68. A method of paragraph 67 wherein the dispersant is colloidal silicon dioxide.
69. A method of any one of paragraphs 59 to 68 wherein the granules comprise about 30, 35, 40, 45, 50, 55, 60, 65 or 70% w/w of the anthelmintic actives.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of preparing a liquid delivery formulation for treating an animal comprising the steps of
    (a) providing one or more packs of multi-active granules, each multi-active granule comprising a combination of a macrocyclic lactone and a gum, a wetting agent, and one or more compositions each including an anthelmintic active and an agent, wherein the one or more compositions are selected from the group consisting of:
        (i) a benzimidazole and a suspending agent for the benzimidazole; and
        (ii) an imidazothiazole and a suspending agent; and
    (b) mixing the multi-active granules from the one or more packs with an aqueous liquid to form a thixotropic or pseudoplastic composition prior to treating the animal;
    wherein each multi-active granule comprises about 30, 35, 40, 45, 50, 55, 60, 65 or 70% w/w of the anthelmintic agents; and
    wherein the multi-active granules, in the one or more packs, are stable for at least 6 months at room temperature.
2. A method of claim 1, wherein a suspending agent is added to the aqueous liquid; or
    wherein the suspending agent is a gum; or
    wherein the aqueous liquid is water: or
    wherein the aqueous liquid is an anthelmintic concentrate; or
    wherein the aqueous liquid contains avermectin and/or milbemycin in a liquid concentrate form; or
    wherein the liquid delivery formulation is suitable for administration to animals for up to one month after mixing; or
    wherein the mixing of each of the multi-active granules with the aqueous liquid is performed at the site of animal administration; or
    further comprising a step before the providing step of determining the treatment needs of one or more animals; or
    further comprising administering the liquid delivery formulation to one or more animals; or
    wherein each multi-active granule comprises
        from about 10 to about 40% w/w benzimidazole, and
        from about 10 to about 60% w/w levamisole HCL; or
    wherein each multi-active granule comprises 15, 20, 25, 30, 35 or 40% w/w macrocyclic lactone; or
    wherein each multi-active granule further comprises a particulate source of one or more minerals; or
    wherein each multi-active granule comprises a suspending agent; or
    wherein each multi-active granule further comprises an anionic surfactant.
3. A method of claim 1 wherein the suspending agent of (a)(i) is a non-colloidal agent.
4. A method of claim 3 wherein the non-colloidal agent is silicon dioxide.
5. A method of forming an anthelmintic composition comprising the steps of:
    providing two or more total anthelmintic actives comprising a macrocyclic lactone and one or more further anthelmintic actives selected from the group consisting of praziquantel, one or more imidazothiazoles, and, one or more benzimidazoles,
    providing a suspending agent, wherein the suspending agent comprises a gum, and mixing the macrocyclic lactone with the suspending agent to form a suspension,
    if the anthelmintic actives comprise a benzimidazole or praziquantel, providing a wetting agent and mixing the benzimidazole or the praziquantel with the wetting agent,
    combining the suspension with the one or more further anthelmintic actives and a wetting agent if a benzimidazole is present to form an anthelmintic active mixture, and
    optionally adding additional suspending agent or rheology modifier comprising a gum, and
    granulating the anthelmintic active mixture to form a granulated combination of multi-active granules each comprising more than one anthelmintic active that has a shelf life of at least 6 months at room temperature, and
    wherein, when subsequently mixed with water the granulated combination of anthelmintic actives forms a stable thixotropic or pseudoplastic mixture.
6. A method of claim 5, further comprising combining a stabilizing agent with the anthelmintic actives prior to granulation.
7. A method of claim 6 wherein the stabilizing agent is a gum; or wherein the granules further comprise a particulate source of one or more minerals; or wherein the granules comprise about 30, 35, 40, 45, 50, 55, 60, 65 or 70% w/w of the anthelmintic actives.
8. The method of claim 5, wherein the granulated combination of anthelmintic actives is stable for at least 6 months.
9. The method of claim 5, wherein the granules further comprise a dispersant.
10. A method of claim 9
    wherein the wetting agent is polysorbate 80; or
    wherein the dispersant is colloidal silicon dioxide.
11. A method of claim 5, wherein a suspending agent is added to the water: or
    wherein the suspending agent is a gum; or
    wherein the water contains avermectin and/or milbemycin in a liquid concentrate form; or
    wherein the thixotropic or pseudoplastic mixture is suitable for administration to animals for up to one month after mixing; or wherein the mixing of each of the multi-active granules with the water is performed at the site of animal administration; or further comprising a step before the providing step of determining the treatment needs of one or more animals; or further comprising administering the thixotropic or pseudoplastic mixture to one or more animals; or wherein each multi-active granule comprises from about 10 to about 40% w/w benzimidazole, and from about 10 to about 60% w/w levamisole HCL: or wherein each multi-active granule comprises 15, 20, 25, 30, 35 or 40% w/w macrocyclic lactone; or wherein each multi-active granule further comprises a particulate source of one or more minerals; or wherein each multi-active granule comprises a suspending agent; or wherein each multi-active granule further comprises an anionic surfactant.

* * * * *